United States Patent
Horn

(10) Patent No.: US 9,902,948 B2
(45) Date of Patent: Feb. 27, 2018

(54) LIBRARY-BASED METHODS AND COMPOSITIONS FOR INTRODUCING MOLECULAR SWITCH FUNCTIONALITY INTO PROTEIN AFFINITY REAGENTS

(71) Applicant: BOARD OF TRUSTEES OF NORTHERN ILLINOIS UNIVERSITY, DeKalb, IL (US)

(72) Inventor: James R. Horn, Sycamore, IL (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 797 days.

(21) Appl. No.: 13/848,547

(22) Filed: Mar. 21, 2013

(65) Prior Publication Data

US 2013/0203609 A1    Aug. 8, 2013

Related U.S. Application Data

(63) Continuation-in-part of application No. PCT/US2011/054021, filed on Sep. 29, 2011.

(60) Provisional application No. 61/388,215, filed on Sep. 30, 2010.

(51) Int. Cl.
| | |
|---|---|
| C40B 30/04 | (2006.01) |
| C12N 15/10 | (2006.01) |
| C07K 16/40 | (2006.01) |
| C07K 16/44 | (2006.01) |
| G01N 33/68 | (2006.01) |

(52) U.S. Cl.
CPC ......... *C12N 15/1037* (2013.01); *C07K 16/40* (2013.01); *C07K 16/44* (2013.01); *G01N 33/6854* (2013.01); *C07K 2317/14* (2013.01); *C07K 2317/22* (2013.01); *C07K 2317/569* (2013.01); *C07K 2317/90* (2013.01); *C07K 2317/92* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 6,668,407 | B1 | 12/2003 | Reitzel |
| 2007/0239225 | A1 | 10/2007 | Saringer |
| 2010/0168395 | A1 | 7/2010 | Sato |
| 2013/0040905 | A1 | 2/2013 | Kratz |
| 2013/0053541 | A1 | 2/2013 | Shankar et al. |
| 2013/0203609 | A1 | 8/2013 | Horn |

FOREIGN PATENT DOCUMENTS

| | | |
|---|---|---|
| AU | 2013204580 | 10/2013 |
| EP | 2275443 | 1/2011 |
| EP | 2423217 | 2/2012 |

(Continued)

OTHER PUBLICATIONS

Alberts (2005) "A wakeup call for science faculty," *Cell* 123, 739-741.

(Continued)

*Primary Examiner* — Christian Boesen
(74) *Attorney, Agent, or Firm* — Barnes & Thornburg LLP; Alice O. Martin

(57) ABSTRACT

Methods and compositions are disclosed for introducing molecular switch functionality into a protein affinity reagent to render its binding to a target molecule sensitive to an environmental trigger, such as pH, while maintaining binding affinity to the target molecule. Combinatorial libraries created by the method are also disclosed.

9 Claims, 18 Drawing Sheets

(56) References Cited

FOREIGN PATENT DOCUMENTS

| | | |
|---|---|---|
| WO | WO 95/14710 | 6/1995 |
| WO | WO 01/44463 | 6/2001 |
| WO | WO 2008/119096 | 10/2008 |
| WO | WO 2009/125825 | 10/2009 |
| WO | WO 2009/139822 | 11/2009 |
| WO | WO 2012/044831 | 4/2012 |

OTHER PUBLICATIONS

Almagro (2004) "Identification of differences in the specificity-determining residues of antibodies that recognize antigens of different size: implications for the rational design of antibody repertoires," *J. Mol Recognit* 17, 132-143.
Alvarez-Rueda et al. (2007) "Generation of llama single-domain antibodies against methotrexate, a protypical hapten," *Mol Immunol.* 44, 1680-1690.
Ambroggio, et al. (2006) "Design of protein conformational switches," *Current Opinion in Structural Biology* 16, 525-530.
Antosiewicz et al., (1994) "Prediction of pH-dependent Properties of Proteins," *J. Mol. Biol.* 238: 415-436.
Ascenzi, et al. (1991) "Binding of the recombinant proteinase inhibitor eglin c from leech *Hirudo medicinalis* to serine (pro)enzymes: a comparaftive thermodymaic study," *J Mol Recognition* 4, 113-119.
Baek, et al. (2002) "An improved helper phage system for efficient isolation of specific antibody moleculares in phage display," *Nucleic Acids Res.* 30, e18.
Baker, et al. (1996) "Evaluation of linked protonation effects in protein binding reactions using isothermal titration calorimetry," *Biophys, J.* 71, 2049-2055.
Baker, et al. (1997) "Dissecting the energetics of a protein-protein interaction: the binding of ovomucoid third domain to elastaste," *J. Mol. Biol* 268, 557-569.
Barbas, et al. (1993) "Selection of human anti-hapten antibodies from semisynthetic libraries," *Gene* 137, 57-62.
Bird, et al (1988) "Single-chain antigen-binding proteins," *Science* 242, 424-426.
Blenner et al., "Characterization of the 4D5Flu Single-Chain Antibody with a Stimulus-Responsive Elastin-Like Peptide Linker: A Potential Reporter of Peptide Linker Conformation," Protein Science, 17:3, 527-536 (2008).
Blond-Elguindi et al., (1993) "Affinity Panning of a Library of Peptides Displayed on Bacteriophages Reveals the Binding Specificity of BiP," *Cell*, 75: 717-728.
Bradbury et al. (2004) "Antibodies from phage antibody libraries," *J Immunol Methods* 290, 29-49.
Brinkmann, et al (1993) "A recombinant immunotoxin containing a disulfide-stabilized Fv fragment," *Proc Natl Acad Sci U S A* 90, 7538-7542.
Buskirk, et al. (2005) "Creating small-molecule-dependent switches to modulate biological functions," *Chem. Biol* 12, 151-161.
Cacciatore, et al. (2008) "Connecting solubility, equilibrium, and periodicity in a green, inquiry experiment for the general chemistry laboratory," *J. Chem. Educ.* 85, 251-253.
Carmen et al., "Concepts in Antibody Phage Display," Briefings in Functional Genomics and Proteomics, 1:2, 189-203 (2002).
Charlton, et al (2001) "The isolation of super-sensitive anti-hapten antibodies from combinatorial antibody libraries derived from sheet," *Biosens Bioelectron* 16, 639-646.
Collis et al (2003) "Analysis of the antigen combining site: correlations between length and sequence composition of the hypervariable loops and the nature of the antigen," *J. Mol Biol* 325, 337-354.
Committee on Prospering in the Global Economy of the 21$^{st}$ Century (U.S.), and Committee on Science Engineering and Public Policy (U.S.)(2007) "Rising above the gathering storm; energizing and employing America for a brighter economic future," *National Academies Press*, Washington, D.C.

Cunningham, et al. (1989) "High-resolution epitope mapping of hGh-receptor interactions by alanine-scanning mutagenesis," *Science* 244, 1081-1085.
Cunningham, et al. (1993) "Comparison of a structural and a functional epitope," *J. Mol Biol* 234, 554-563.
Damberger et al. (2000) NMR characterization of a pH-dependent equilibrium between two folded solution conformations of the pheromone-binding protein from *Bombyx mori, Protein Science*, 9, 1038-1041.
Decanniere et al. (1999) "A single-domain antibody fragment in complex with RNase A: non-canonical loop structures and nanomolar affinity using two CDR loops," *Structure*, 7:4, 361-370.
Ding et al. (2001) "Size-dependent control of the binding of biotinylated proteins to streptavidin using a polymer shield," *Nature*, 411, 59-62.
Doster et al. et al. (1982) "Control and pH Dependence of Ligand Binding to Heme Proteins," *Biochemistry* 21:20, 4831-4839.
Doyle, et al. (2008) "Cloning, expression, and characterization of a single-domain antibody fragment with affinity for 15-acetyl-deoxynivalenol," *Mol. Immunol.* 45, 3703-3713.
Edgcomb, et al. (2000) "The energetics of phosphate binding to a protein complex," *Protein Sci* 9, 927-933.
Eftink, et al. (1983) "Enthalpy-entropy compensation and heat capacity changes for protein-ligand interactions; general thermodynamic models and data for the binding of nucleotides to ribonuclease A," *Biochemistry* 22, 3884-3896.
Ericsson, et al. (2006) "Thermofluor-based high-throughput stability optimization of proteins for structural studies," *Anal Biochem* 357, 289-298.
Feig, et al (2002) "Incorporation of bioinformatics exercises into the undergraduate biochemistry curricumulum," *Biochemistry and Molecular Biology Education* 30, 224-231.
Fellouse, et al (2006) "Tyrosince plays a dominant functional role in the paratope of a synthetic antibody derived from a four amino acid code," *J. Mol Biol* 357, 100-114.
Fellouse, et al. (2004) "Synthetic antibodies from a four-amino-acid code, a dominant role for tyrosine in antigen recognition," *Proc Natl Acad Sci U S A* 101, 12467-12472.
Fellouse, et al. (2005) "Molecular recognition by a binary code," *J Mol Biol* 348, 1153-1162.
Fellouse, et al. (2007) "High-throughput Generation of Synthetic Antibodies from Highly Functional Minimalist Phage-displayed Libraries," *J Mol Biol* 373, 924-940.
Fitch, et al. (2006) "Molecular mechanisms of pH-driven conformational transitions of proteins: Insights from continuum electrostatics calculations of acid unfolding," *Protein* 63, 113-126.
Franco, et al. (2009) "Production and characterization of a genetically engineered anti-caffeine camelid antibody and its use in immunoaffinity chromatography," *Journal of Chromatography B—Analytical Technologies in the Biomedical and Life Sciences in Press*, doi:10.1016/j.jchromb.2009.1006.1017.
Gani, et al. (1994) "Monoclonal-Antibodies against Progesterone-Effect of Steroid-Carrier Coupling Position on Antibody Specificity," *Journal of Steroid Biochemistry and Molecular Biology*, 48, 277-282.
Georgiou, et al. (1997) "Display of heterologous proteins on the surface of microorganisms: from the screening of combinatorial libraries to live recombinant vaccines," *Nat. Biotechnol* 15, 29-34.
Gerstner et al. (2002) "Sequence plasticity in the antigen-binding site of a therapeutic anti-HER2 antibody," *J. Mol Biol* 321, 851-862.
Gilbreth, et al. (2008) "A dominant conformational role for amino acid diversity in minimalist protein-protein interfaces," *J. Mol Biol* 381, 407-418.
Green, et al. (2004) "Prompted" inquiry-based learning in the introductory chemistry laboratory, *J. Chem. Educ.* 81, 239-241.
Griffiths, et al. (1994) "Isolation of high affinity human antibodies directly from large synthetic repertoires," *Embo J.* 13, 3245-3260.
Hamers-Casterman, et al. (1993) "Naturally occurring antibodies devoid of light chains," *Nature* 363, 446-448.
Harms et al., (2008) "A buried lysine that titrates with a normal pK(a): Role of conformational flexibility at the protein-water interface as a determinant of pK(a)values," *Protein Sci.* 17, 833-845.

(56) References Cited

OTHER PUBLICATIONS

Henkels, et al. (2001) "Linked folding and anion binding of the Bacillus subtilis ribonuclease P protein," *Biochemistry* 40, 2777-2789.

Higaki, et al. (1992) "Engineered metalloregulation in enzymes," *Trends Biochem Sci* 17, 100-104.

Hoogenboom, "Selecting and screening recombinant antibody libraries," *Nat Biotechnol* 23, 1105-1116 (2005).

Horn, et al. (2003) "Structure and energetics of protein-protein interactions: the role of conformational heterogeneity in OMTKY3 binding to serine proteases," *J. Mol. Biol.* 331, 497-508.

International Search Report and Written Opinion of PCT/US2011/054021 dated Nov. 29, 2011.

Isom et al. (2008) "High tolerance for ionizable residues in the hydrophobic interior of proteins," *PNAS*, 105:46, 17784-17788.

Isom et al. (2010) "Charges in the hydrophobic interior of proteins," *PNAS*, 107:37, 16096-16100.

Isom et al. (2011) "Large Shifts in $pK_a$ values of lysine residues buried inside a protein," *PNAS*, 108:13, 5260-5265.

Ito et al., "The Hisprobe Method Effects of Histidine Residues Introduced Into the Complementarity-Determining Regions of Antibodies on Antigen-Antibody Interactions at Different PH Values," Feb Letters, 309:1, 85-88 (1992).

Jespers, et al. (2004) "Crystal structure of HEL4, a soluble, refoldable human V(H) single domain with a germ-lined scaffold," *J. Mol. Biol.* 337, 893-903.

Kimbrough, et al. (1997) "A laboratory experiment investigating different aspects of catalase activity in an inquiry-based approach," J. Chem. Educ. 74, 210-212.

Knappik, et al. (2000) "Fully synthetic human combinatorial antibody libraries (HuCAL) based on modular consensus frameworks and CDRs randomized and trinucleotides," *J. Mol. Biol* 296, 57-86.

Koide et al., (2007) "Exploring the capacity of minimalist protein interfaces: interface energetics and affinity maturation to picomolar KD of a single domain antibody with a flat paratope," *J. Mol. Biol.*, 373(4): 941-953.

Koide, et al (1998) "The fibronectin type III domain as a scaffold for novel binding proteins," *J. Mol Biol* 284, 1141-1151.

Koide, et al (2007) "High-affinity single-domain binding proteins with a binary-code interace," *Proc Natl Acad Sci U S A* 104, 6632-6637.

Koide, et al. (2009) "The importance of being tyrosine: lessons in molecular recognition from minimalistic synthetic binding proteins," *ACS Chem Biol* 4, 325-334.

Kouadio, et al. (2005) "Shotgun alanine scanning shows that growth hormone can bind productively to its receptor through a drastically minimized interface," *J. Biol Chem.* 280, 25524-25532.

Krantz et al. (2001) "Engineered metal binding sites map the heterogeneous folding landscape of a coiled coil," *Nat. Struct. Biol.* 8, 1042-1047.

Kundrotas, et al (2006) "Electrostatic properties of protein-protein complexes," *Biophys J.* 91, 1724-1736.

Ladenson, et al. (2006) "Isolation and characterization of a thermally stable recombinant and-caffeine heavy-chain antibody fragment," *Anal Chem* 78, 4501-4508.

Lahiri, et al (1999) "A strategy for the generation of surfaces presenting ligands for studies of binding based on an active ester as a common reactive intermediate: a surface plasmon resonance study," *Anal Chem* 71, 777-790.

Leckband , "Measuring the Forces That Controlprotein Interactions," *Annu. Rev. Biophys.*, 29:1-26 (2000).

Lipovsek et al. (2004) "In-vitro protein evolution by ribosome display and mRNA display," *J Immunol Methods* 290, 51-67.

Lowman et al. (1991) "Selecting High-Affinity Binding Proteins by Monovalent Phage Display," *Biochemistry*, 30, 10832-10838.

Lu, et al. (2001) "Engineering novel metalloproteins: Design of metal-binding sites into native protein scaffolds," *Chemicals Reviews* 101, 3047-3080.

MacDonald, (2008) "Teaching Protein Purification and Characterization Techniques: A student-Initiated, Project-Oriented Biochemisry Laboratory Course," *J. Chem. Educ.* 85, 3.

Mason, et al (2008) "Protein-protein binding is often associated with changes in protonation state," *Proteins* 71, 81-91.

McGrath, et al. (1993) "Structure of an engineered, metal-actuated switch in trypsin," *Biochemistry* 32, 1914-1919.

Murtaugh et al., "A Combinatorial Histidine Scanning Library Approach to Engineer Highly pH-Dependent Protein Switches," *Protein Science*, 20 1619-1631 (2011).

Nguyen, et al. (1998) "The specific variable domain of camel heavy-chain antibodies is encoded in the germline," *J Mol Biol* 275, 413-418.

Otwinowski et al., "Processing of X-Ray Diffraction Data Collected in Oscillation Mode," In *Methods in enzymology: Macromolecular crystallography, part A*. (eds. C.W. Carter Jr and R.M. Sweet). vol. vol. 276, pp. 307-326. Academic Press, New York (1997).

Pace et al., "How to measure and predict the molar absorption coefficient of a protein," *Protein Science*, 4:2411-2423 (1995).

Persson, et al. (2006) "A focused antibody library for improved hapten recognition," *J. Mol Biol.* 357, 607-620.

Perutz, et al. (1980) "Identification of Residues Contributing to the Bohr Effect of Human-Hemoglobin," *J Mol. Biol.* 138, 649-670.

Reiersen, et al. (2005) "Covalent antibody display—an in vitro antibody-DNA library selection system," *Nucleic Acids Res.* 33, e10.

Rodewald, (1976) "pH-Dependent Binding of Immunoglobulins to Intestinal Cells of the Neonatal Rat," *J. of Cell Biol.*, 71, 666-670.

Sagermann et al., "Using Affinity Chromatography to Engineer and Characterize PH-Dependent Protein Switches," *Protein Science*, 18:1 217-228 (2009).

Sarkar, et al. (2002) "Rational cytokine design for increased lifetime and enhanced potency using pH-activated histidine switching," *Nat. Biotechnol* 20, 908-913.

Sheedy et al., "Isolation and affinity maturation of hapten-specific antibodies," *Biotechnol Adv.*, 25: 333-352 (2007).

Sheinerman et al. (2002) "On the role of electrostatic interactions in the design of protein-protein interfaces," *J. Mol Biol* 318, 161-177.

Sidhu et al. (2004) "Phage-displayed antibody libraries of synthetic heavy chain complementarity determining regions," *J. Mol. Biol.* 338, 299-310.

Sidhu et al., (2004), "Constructing phage display libraries by oligonucleotide-directed mutagenesis," in *Phage Display: a practical approach* (Clarkson, T. and Lowman, H.B. Eds.) pp. 27-41, Oxford University Press.

Sidhu, et al. (2000) "Phage display for selection of novel binding peptides," *Methods Enzymol* 328, 333-363.

Sidhu, et al. (2006) "Synthetic therapeutic antibodies," *Nat. Chem. Biol.* 2, 682-688.

Smith (1985) "Filamentous fusion phage: novel expression vectors that display cloned antigens on the virion surface," *Science* 228, 1315-1317.

Sonneson, et al. (2009) "Hapten-Induced Dimerization of a Single-Domain VHH Camelid Antibody," *Biochemistry* 48, 6693-6695.

Spinelli, et al. (2001) "Lateral recognition of a dye hapten by a llama VHH domain," *J Mol Biol* 311, 123-129.

Syme et al. (2004) "Cooper Binding to the Amyloid-β (Aβ) Peptide Associated with Alzheimer's Disease," *J. of Biological Chem.*, 279:18, 18169-18177.

Tawfik et al. (1994) "Ph on-Off Switching of Antibody Hapten Binding by Site-Specific Chemical Modification of Tyrosine," *Protein Engineering* 7, 431-434.

Taylor, et al.(2007) "Bringing the excitement of biologicl research into the chemistry classroom at MIT," *ACS Chemical Biology* 2, 515-517.

Turnbull et al. "On the Value of c: Can Low Affinity Systems Be Studied by Isothermal Titration Calorimetry?," *J. Am. Chem. Soc.*, 125: 14859-14866 (2003).

Vajdos, et al. (2002) "Comprehensive functional maps of the antigen binding site of an anti-ErbB2 antibody obtained with shotgun scanning mutagenesis," *J Mol Biol* 3210, 415-428.

(56) References Cited

OTHER PUBLICATIONS

Vincent, et al. (1973) "The interaction between alpha-chymotrypsin and pancreatic trypsin inhibitor (Kunitz inhibitor). Kinetic and thermodynamic properties," *Eur J Biochem* 38, 365-372.
Waldrop, (2008) "Science 2.0," *Sci Am* 298, 68-73.
Watanabe, et al. (2009) "Optimizing pH Response of Affinity between Protein G and IgG Fc: How Electrostratic Modulations Affect Protein-Protein Interactions," *J. Biol. Chem.* 284, 12373-12383.
Weiss, et al. (2000) "Rapid mapping of protein functional epitopes by combinatorial alanine scanning," *Proc Natl Acad Sci U.S.A.* 97, 8950-8954.
Whitlow, et al. (1993) "An improved linker for single-chain Fv with reduced aggregation and enhanced proteolytic stability," *Protein Eng* 6, 989-995.
Willett, et al. (1995) "Engineered metal regulation of trypsin specificity," *Biochemistry* 34, 2172-2180.
Wittrup (2001) "Protein engineering by cell-surface display," *Curr Opin Biotechnol* 12, 395-399.
Yau, et al. (2003) "Selection of hapten-specific single-domain antibodies from a non-immunizeed llama ribosome display library," *J Immunol. Methods* 281, 161-175.
Applicant response dated Oct. 29, 2013 in response to Art. 94(3) Communication filed in examination of the opposed patent (EP 2622074).
Applicant submission dated Feb. 29, 2012 made during international examination under Chapter II proceedings.
Article 94(3) EPC Communication dated Jul. 31, 2013 issued in examination of the opposed patent (EP 2622074).
Desmyter et al., "Three Camelid VHH Domains in Complex with Porcine Pancreatic alpha-Amylase," *The Journal of Biological Chemistry*, 277(26): 23645-23650 (Apr. 17, 2002).
Horn et al., "Interface Histidine Scanning of a Protein Interface to Modulate Protein-Protein Binding," *Protein Science*, 19(S1): 250 (Jul. 2010) (Abstr.).
Horn, Curriculum Vitae, Downloaded Jul. 6, 2015 from http://www.niu.edu/chembio/directory/cv/Horn_CV15.pdf.
Horn, Lab News Archives Downloaded Jul. 6, 2015 from http://hornlab.niu.edu/pmwiki/pmwiki.php/Main/NewsArchives.
Martin, Information provided by website of Dr. Andrew C.R. Martin, downloaded Jul. 26, 2015 from http://www.bioinf.org.ukJabs/.
Opposition submitted in Pat. No. EP2622074 (Jul. 29, 2015).
Protein Science, 24th Annual Symposium, vol. 19, Issue S1 (Jul. 2010), online publication information. Downloaded Jul. 15, 2015 from http://onlinelibrary.wiley.com/doi/1 0.1002/pro.448/abstract.

$K_{obs} = K_1(1+K_2[VHH2])$

US 9,902,948 B2

LIBRARY-BASED METHODS AND COMPOSITIONS FOR INTRODUCING MOLECULAR SWITCH FUNCTIONALITY INTO PROTEIN AFFINITY REAGENTS

This application is a continuation-in-part of copending International Application No. PCT/US2011/054021, filed Sep. 29, 2011, which claims priority to U.S. provisional application No. 61/388,215, filed Sep. 30, 2010. The disclosures set forth in the referenced applications are incorporated herein by reference in their entireties, including all information as originally submitted to the United States Patent and Trademark Office.

The United States Government has rights in this invention pursuant to NSF No. MCB-0953323 between the United States Government and the Board of Trustees for Northern Illinois University.

SEQUENCE LISTING

The instant application contains a Sequence Listing which has been submitted in ASCII format via EFS-Web and is hereby incorporated by reference in its entirety. Said ASCII copy, created on Jun. 11, 2015, is named 700849_Amd_SEQ_ST25.txt and is 13,268 bytes in size.

BACKGROUND

Methods and compositions are disclosed to control function of protein affinity reagents by integrating molecular switches into the structure of the reagents without deleteriously affecting the ability of the reagents to bind to their target molecules.

Protein affinity reagents are proteins which bind with high affinity to specific target molecules, such as proteins, nucleic acids, and small molecules such as a haptens or drugs, with high affinity and specificity. Antibodies are the best known example of protein affinity reagents, but the class also includes antibody fragments, fibronectins, ankyrin repeats, and armadillo proteins. Advances in protein engineering have led to the development of modified protein affinity reagents with properties not found in nature.

Antibodies are widely used as biological affinity reagents in therapeutics and diagnostics, as imaging agents, and as affinity purification agents in fundamental research and industrial applications. They have also served as useful models in understanding fundamental structure/function relationships for protein-protein binding.

A useful modification of a protein affinity reagent is the introduction of molecular switch functionality, that is, the ability to respond to a specific environmental trigger with an alteration in target binding affinity. Antibodies with this characteristic can bind or release an antigen or other bound target molecule, such as a drug, under certain physiological conditions, such as the microenvironment characteristic of a particular disease or tissue, or at specific steps of an affinity purification process.

Attempts to engineer molecular switches have focused on modifications of existing biologically-relevant protein affinity reagents. Only a handful of examples exist that introduce novel molecular control into existing structures. Some success has been achieved in introducing pH dependent binding into antibodies, for example by covalent modification (through nitration) of an antibody/antigen interface or by structure-based molecular modeling. Results for these conventional methods so far, however, have been modest.

SUMMARY OF THE DISCLOSURE

Methods and compositions are disclosed to control function of protein affinity reagents without deleteriously affecting their ability to bind to target molecules. The method does not require knowledge of the 3-dimensional structure of the protein. A combinatorial library is produced, which is then subjected to dual selection for binding and for the environmental response.

A method is disclosed for introducing molecular switch functionality into an existing protein affinity reagent, also called a wild type protein affinity reagent, that binds a target molecule via a target binding interface, the method including:

(a) obtaining an ionizable residue-scanning expression display library of the protein affinity reagent, the library comprising all possible combinations of amino acid residue(s) of the target binding interface wherein each residue position was modified as an ionizable amino acid residue, and the remaining interface positions maintained wild type residues;

(b) selecting a target binding population of reagents from the library based on their ability to bind the target molecule;

(c) selecting a target binding subpopulation from the target binding population that exhibits binding to the target molecule sensitive to an environmental trigger; and (d) identifying a modified target binding reagent from the subpopulation with molecular switch functionality sensitive to the environmental trigger, but maintaining affinity for the target molecule.

The ionizable amino acid residues are added to create sensitivity to environmental triggers; wild type residues are needed to maintain target molecule affinity.

The protein affinity reagent identified may be an antibody, a heavy chain variable domain antibody (VHH), or other proteins which have target molecule interfaces.

Suitable target molecules include a metal ion, where the target binding interface binds the metal ion, a protein, e.g. an antigen, or a low-molecular weight molecule, e.g. a hapten. Additional target molecules could be DNA, RNA, carbohydrates. The target binding interface may include, for example, between about 10 and about 35 amino acid residues in length.

The modification of the amino acids may be done by substitution, insertion, deletion and/or chemical modification.

Histidine residues are suitable ionizable residues to introduce into the target binding interface. Other amino acid residues include: aspartate, arginine, glutamate, and combinations thereof.

A suitable environmental trigger includes a specific pH range.

The equilibrium binding affinity constant, expressed in Kd, of the modified protein to the target molecule is, for example, $10^{-4}$ M to $10^{-12}$ M.

The method further includes:

(e) producing a modified reagent in a suitable prokaryotic, eukaryotic or in vitro expression system, or by chemical synthesis.

A method for producing a protein affinity reagent that binds a target molecule in the presence of a specific pH value or range, includes:

(a) determining binding activity of the protein affinity reagent to the target molecule at the specific pH value or range;

(b) determining binding activity of the protein affinity reagent to the target molecule at less than or greater than the specific pH value or range;

(c) selecting at least one protein affinity reagent on the basis of whether the reagent binds to the target molecule at the specific pH value range and remains unbound to the target molecule at less than or greater than the specific pH value or range; and (d) producing the reagent in a suitable prokaryotic, eukaryotic or in vitro expression system, or by chemical synthesis.

The selected reagent may then be isolated by a suitable purification method.

A library of protein affinity reagents is prepared by repeating steps a-d. The library may be an antibody library.

A gene encoding the reagent selected is identified, and the protein may be produced using the gene.

A method of selecting a population of protein affinity reagents with a molecular environmental switch from the library includes:

(a) contacting the library with a target molecule to form binding complexes in the presence of an environmental trigger;

(b) separating the binding complexes from unbound library protein affinity reagents;

(c) eluting a population of reagents from the binding complexes; and (d) selecting the population of eluted reagents on the basis of the ability to bind the target molecule in the presence of a specific environmental trigger and remain unbound in the absence of the environmental trigger.

A synthetic combinatorial nucleic acid library encoding protein affinity reagents is disclosed that includes reagents with molecular switch functionality sensitive to an environmental trigger, and a target binding interface, wherein the reagents include a plurality of ionizable amino acid residues of the target binding interface, and the reagents bind or release a target molecule in the presence of the environmental trigger. The nucleic acids may be DNA or mRNA.

The reagents are useful for the diagnosis, prophylaxis and treatment of diseases in which the target molecule is directly or indirectly involved. The reagents are useful for the affinity purification and recovery of molecules under designed environmental conditions.

A select population of the library may be produced in a suitable prokaryotic, eukaryotic or in vitro expression system, or by chemical synthesis.

A method for controlling the binding and release of a target molecule by a protein affinity reagent by means of an environmental trigger, includes (a) providing a protein affinity reagent including a molecular switch motif rendering the affinity of the protein affinity reagent sensitive to the environmental trigger, (b) providing the target molecule, (c) incubating the protein affinity reagent with the target molecule, and (d) regulating the presence of the environmental trigger.

A method for generating a protein affinity reagent specific for a hapten includes (a) providing an expression display library of variable antibody domains, (b) selecting a first variable antibody domain that specifically binds a first site on the hapten forming a first variable antibody domain-hapten complex, (c) capturing the first variable antibody domain-hapten complex; (d) selecting a second variable antibody domain which specifically binds the first variable antibody domain-hapten complex, (e) forming a second variable antibody domain-hapten complex including the first variable antibody domain-hapten complex and the second variable antibody domain, and (f) identifying the combination of the first variable antibody domain and the second variable antibody domain as a protein affinity reagent specific for the hapten. For example, the antibody domains may be the VHH domains of camelid single chain antibodies.

BRIEF DESCRIPTION OF THE DRAWINGS

Other aspects of the present disclosure will be readily appreciated as the same becomes better understood by reference to the following detailed description when considered in connection with the accompanying illustrative drawings, which are not necessarily drawn to scale, wherein.

Figure 6:
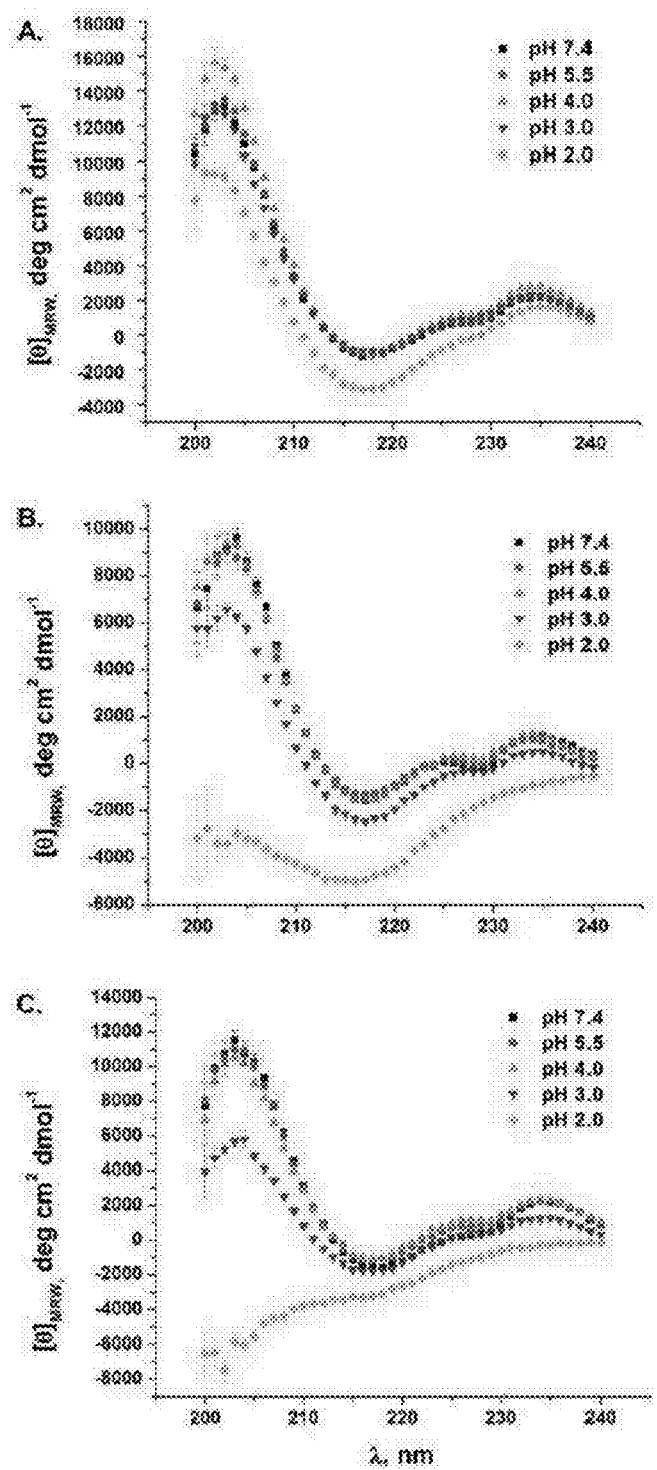
Figure 7:
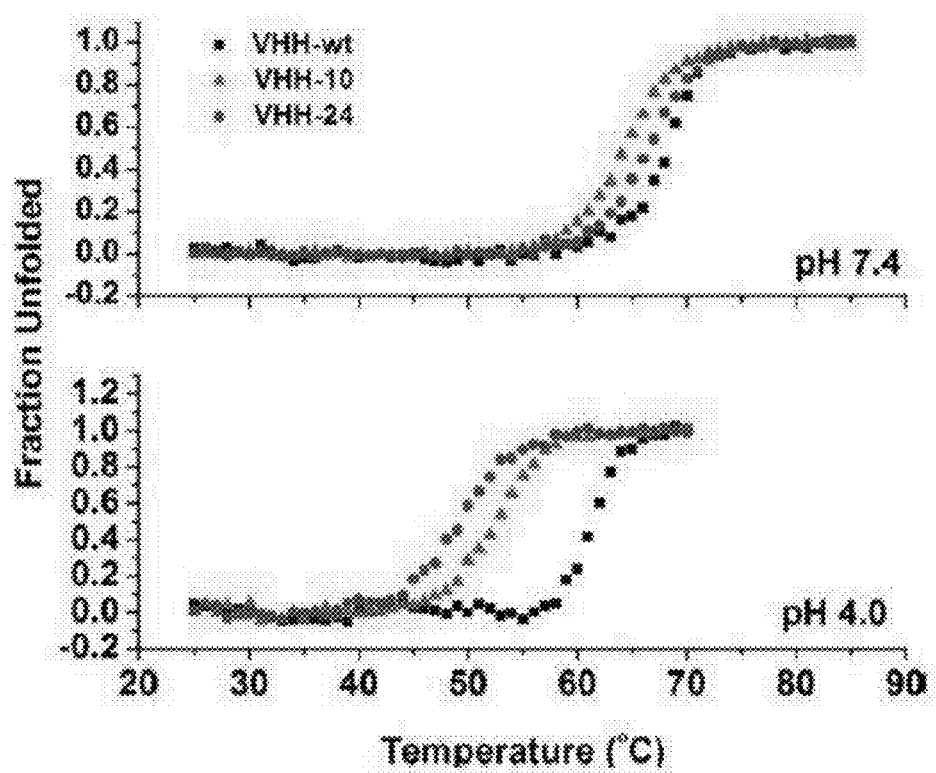
Figure 8:
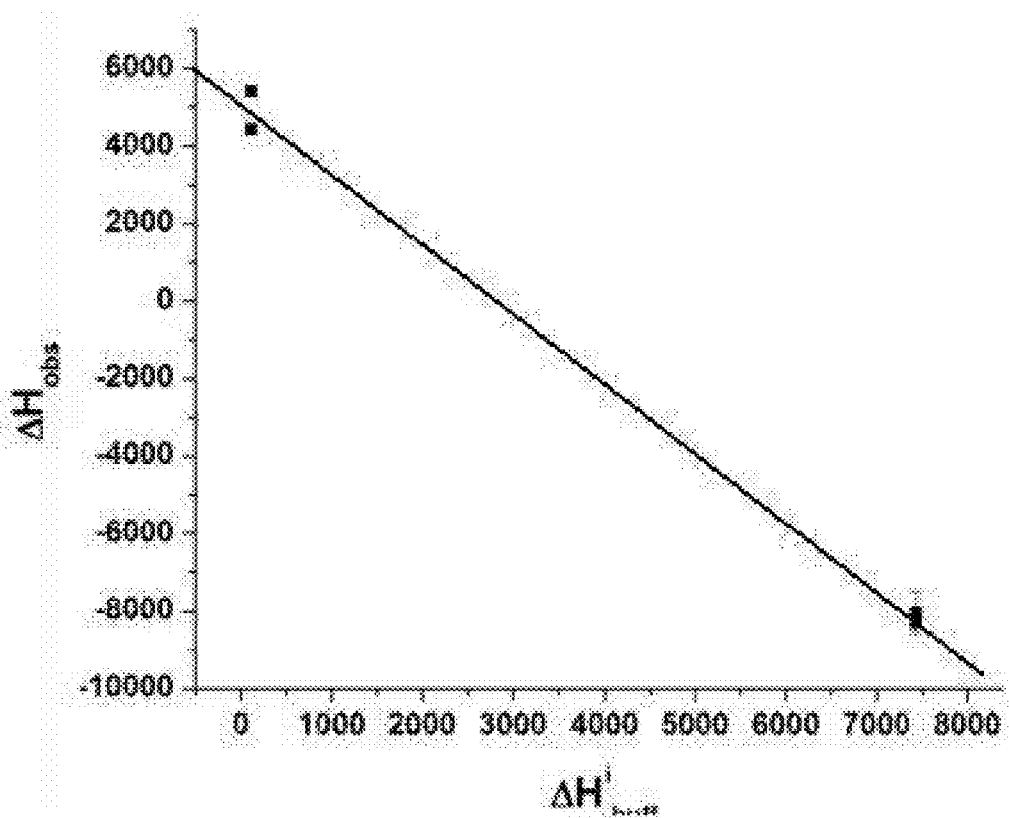
Figure 9:
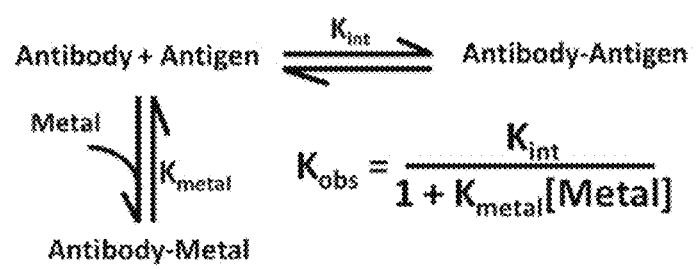
Figure 10:
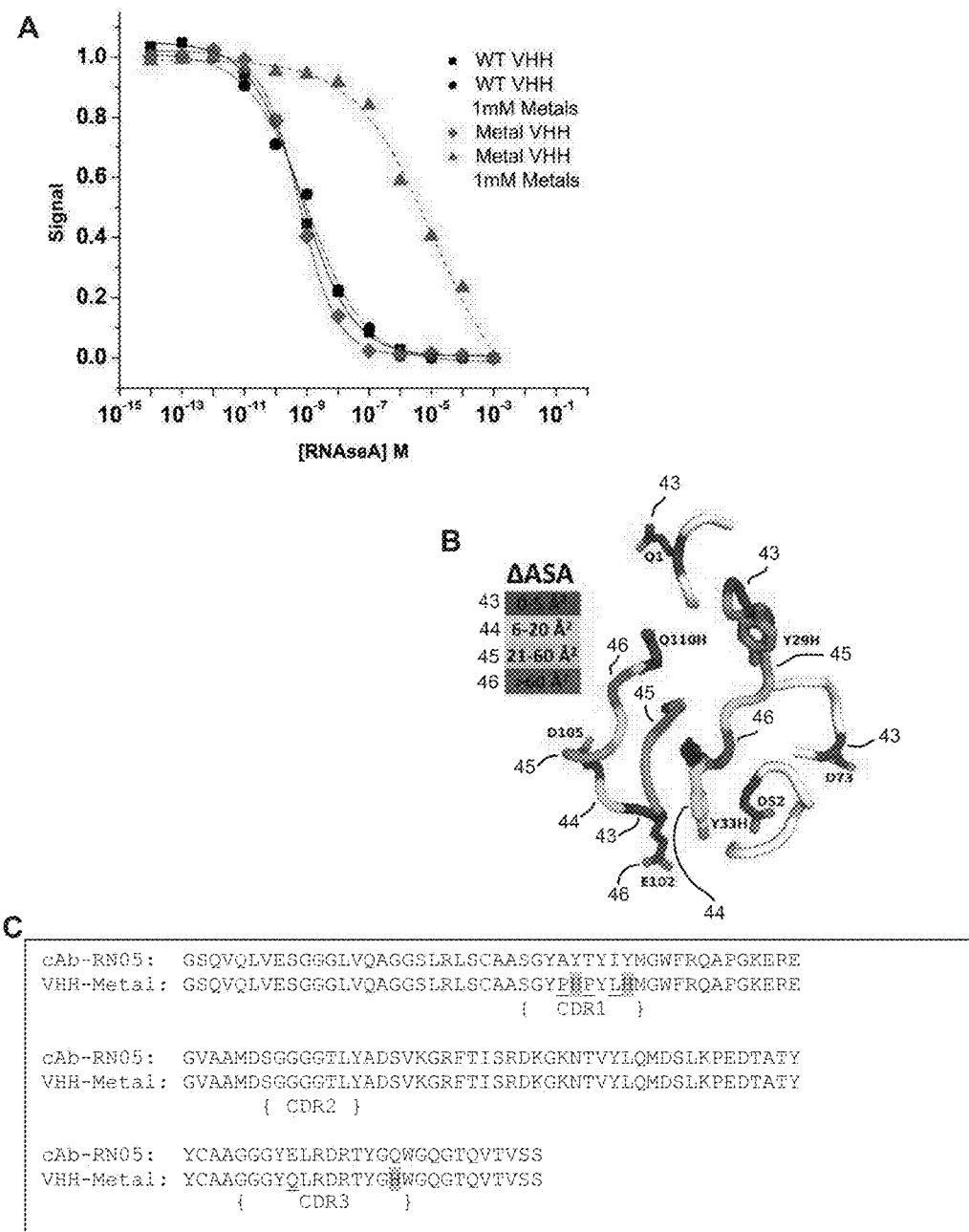
Figure 11:
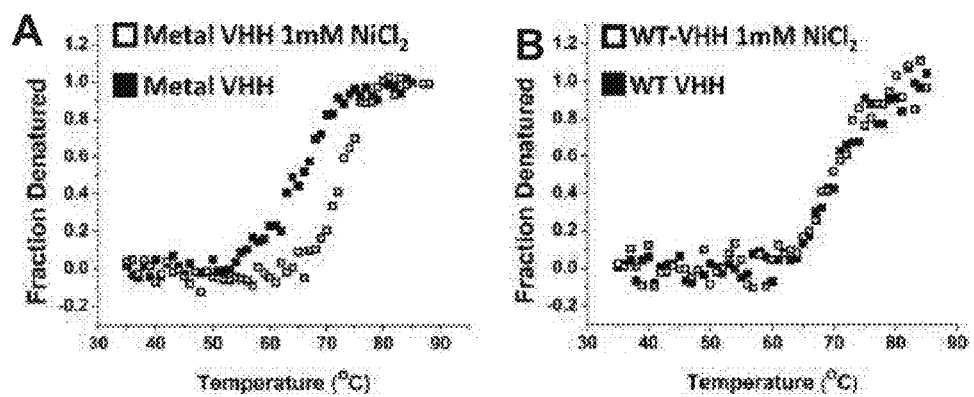
Figure 12:
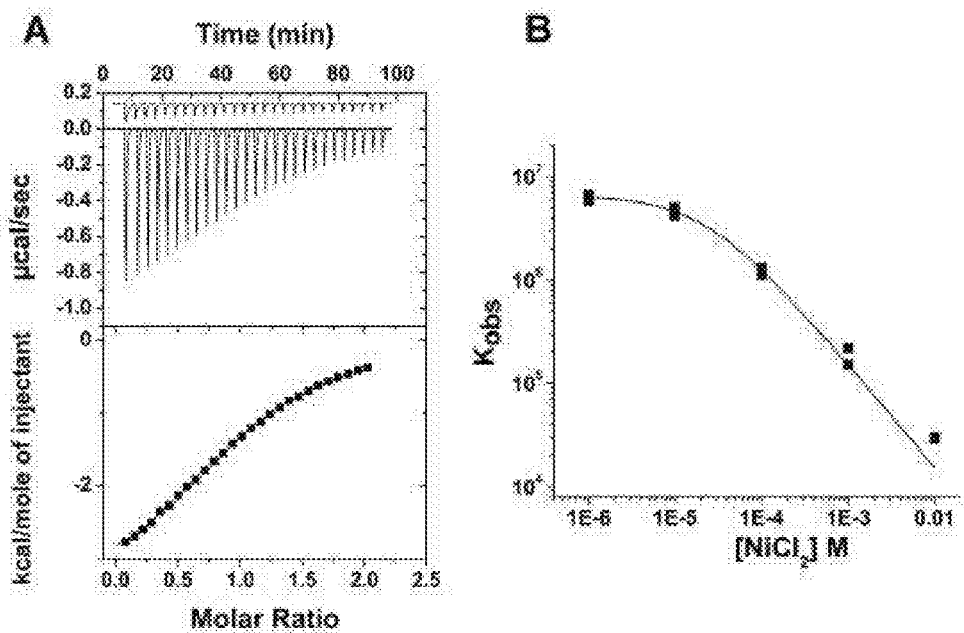
Figure 13:
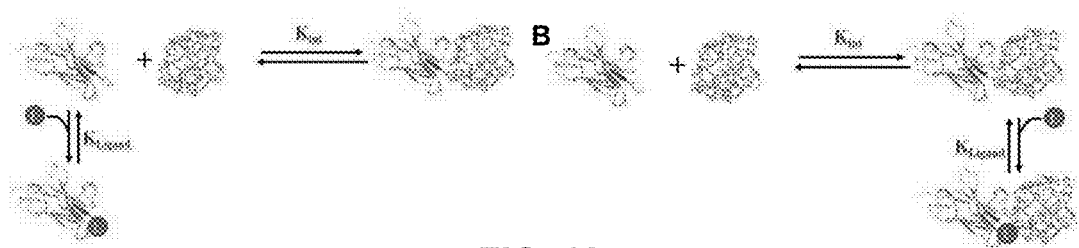
Figure 14:
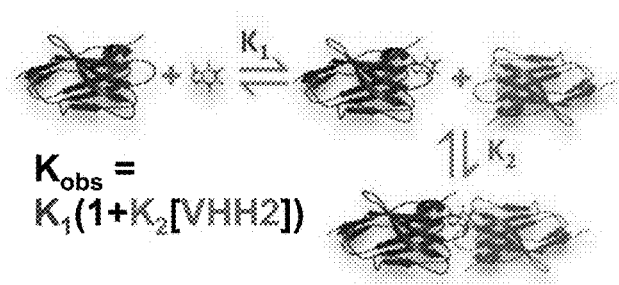
Figure 15:
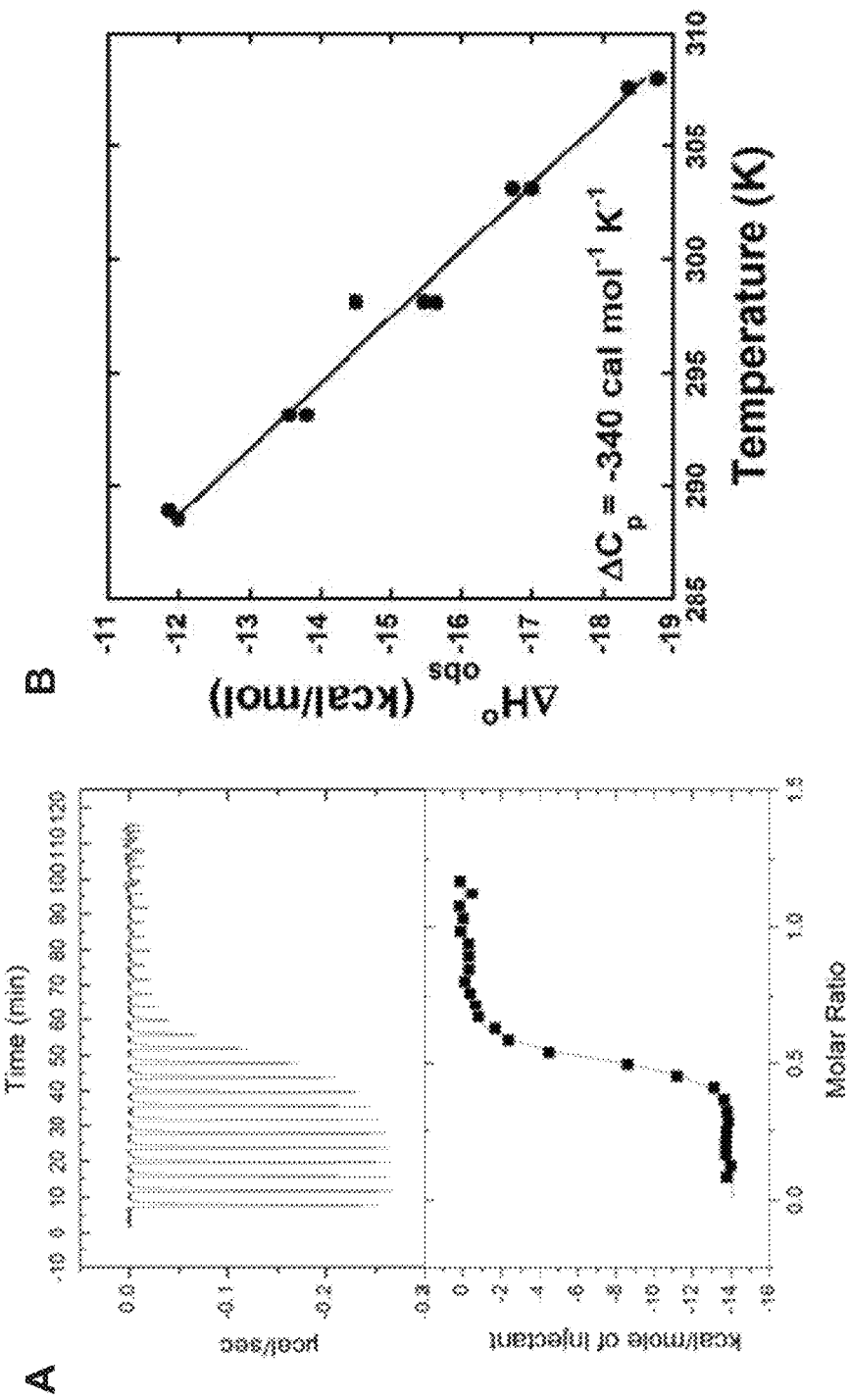
Figure 16:
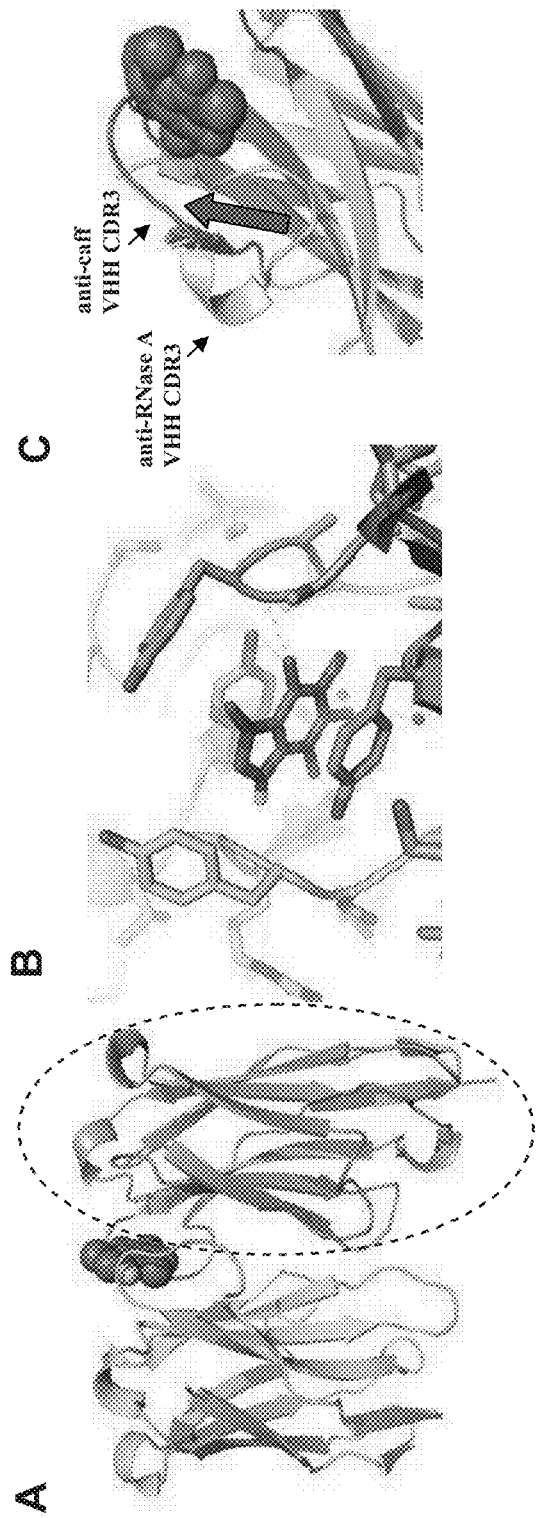

[(3); PDB ID: 2P49] and VHH#24 [(2); PDB ID: 3QSK] RNase A complexes, with RNase A residues displayed in white (1);

FIGS. 6A to 6C show CD spectra as a function of pH for VHH-wt (A), VHH#10 (B) and VHH#24 (C);

FIG. 7 shows temperature unfolding curves of the wild-type VHH, VHH#10, and VHH#24 at pH 7.4 and 4.0;

FIG. 8 shows a plot illustrating the relationship between the observed binding enthalpy, $\Delta H°_{obs}$, and buffer ionization enthalpy, $\Delta H^i_{obs}$, for VHH#10; the slope (−1.78±0.03) of the linear fit indicates the number of protons "released" by the buffer; buffer dependence experiments were run at pH 5.0, 10° C. and contained 150 mM NaCl and 20 mM sodium acetate or piperazine;

FIG. 9 shows a linked-equilibria model for a dual-binding anti-RNase A VHH;

FIG. 10A shows a graph of the results of a competitive ELISA of wild-type and metal sensitive selected clone under conditions with and without 1 mM metal;

FIG. 10B shows an interface view of anti-RNase A VHH, with potential metal binding residues shown as sticks and with positions coded (43-46) according to the change in accessible surface area upon binding RNase A; and with values based on the wild-type anti-RNase A VHH-RNase A complex structure;

FIG. 10C shows a sequence alignment of the anti-RNase A VHH (cAB-RN05 (SEQ ID NO: 43)) and metal sensitive anti-RNase A VHH (VHH-metal (SEQ ID NO: 44)); with amino acid positions that were changed to histidine shown highlighted in grey, while sequence changes to another non-wt-residues are underlined;

FIGS. 11A and 11B show thermal unfolding of the VHH-metal variant (A) and wild-type anti-RNase A (B), respectively, with and without 1 mM $Ni^{2+}$;

FIG. 12A shows the data from ITC titration of nickel into the metal binding VHH-metal (200 μM); dilution heats are offset in the top panel;

FIG. 12B shows the observed binding constant for VHH-metal as a function of nickel concentration; line is a non-linear fit to a single site metal binding model;

FIG. 13 shows coupled equilibria schemes where ligand binding to either the free (A) or complex (B) state results in a ligand dependent decrease or increase in affinity, respectively, Kint, represents the intrinsic antibody/antigen binding constant and KLigand is the affinity of the ligand for the antibody or antibody/antigen complex, generic "ligand" represented by a circle with an L inside;

FIG. 14 shows a coupled equilibria scheme for dual VHH hapten recognition, where the initial 1:1 hapten/VHH complex serves as the target for a second site VHH domain, thereby allowing formation of a 2:1 complex, and as a consequence, the observed binding constant for hapten complexes is dependent on both stepwise binding constants and the free concentration of the second VHH binding domain;

FIG. 15A shows the results of a representative ITC experiment for an anti-caffeine/VHH complex;

FIG. 15B shows the determination of the binding $\Delta C_p$ by ITC;

FIG. 16A shows a ribbon structure of the 2:1 VHH: caffeine complex, the VHH domains display two-fold symmetry. A single VH domain is found within the dotted oval. Caffeine is shown in spheres (top-center location of panel A);

FIG. 16B shows caffeine "sandwiched" between the two VHH domains with CDR3 participating in key interactions with caffeine; and FIG. 16C is a close-up of a single VHH domain which illustrates CDR3 loop displacement from its canonical position when bound to caffeine.

Figure 17:
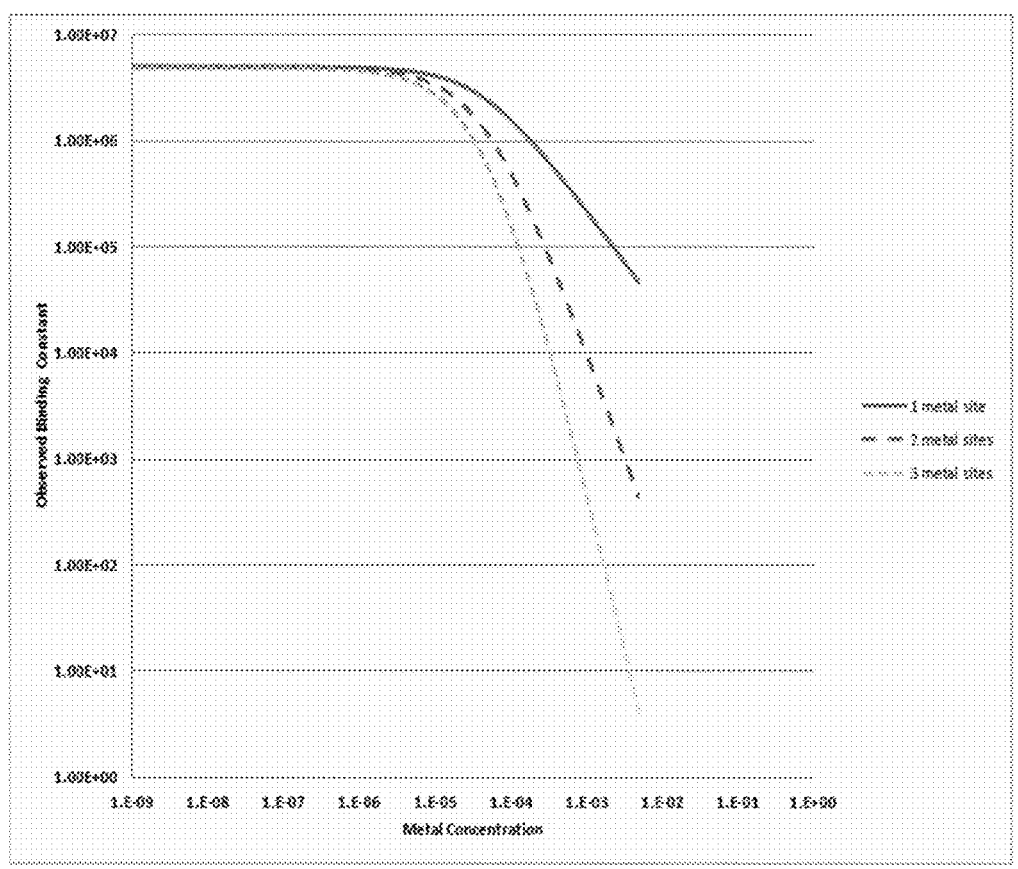

FIG. 17 shows results of simulation of the dependence of the protein binding constant as a function of metal which demonstrates the enhanced sensitivity resulting from multiple metal binding sites (1, 2, 3).

Figure 18:
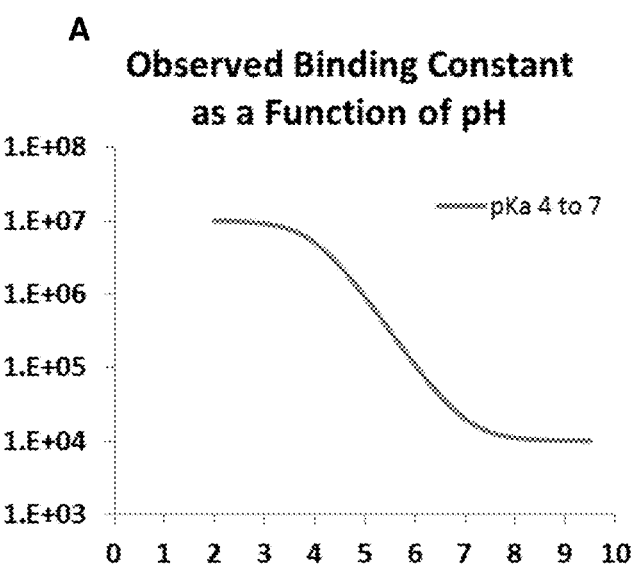
Figure 18:
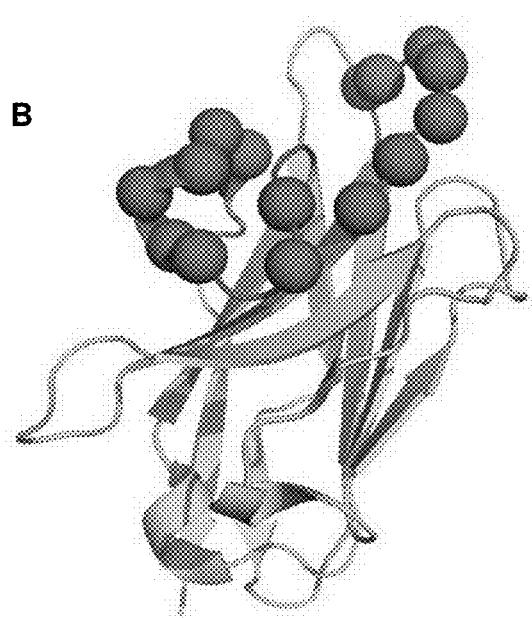

FIG. 18 A) Thermodynamic simulation of the linked-protonation equilibria describing an example of an inverse pH sensitive protein switch. The simulation models a single, ionizable residue undergoing a $pK_a$ increase from 4 to 7 between the free and complex VHH states, respectively. B) Ribbon structure of the anti-RNase A VHH antibody. Grey spheres indicate the 15 Asp/Glu/Wt interface residues (alpha carbons).

Figure 19:
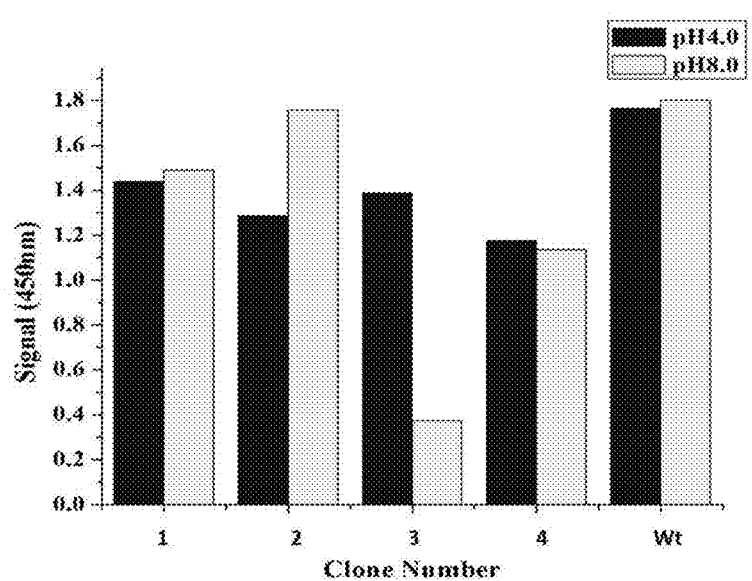

FIG. 19: pH-dependent ELISA screening revealed an inverse pH-sensitive VHH variant. Variant#3 displayed the inverse switch binding profile.

DETAILED DESCRIPTION

Methods and compositions are disclosed for introducing molecular switch functionality into protein affinity reagents, and to identify the molecular switch motifs responsible for that functionality.

The molecular switch functionality is based on the principle of coupled equilibria. Coupled equilibria form the backbone of biological regulation. Proton binding is a classic example, which underlies such phenomena as the Bohr effect in hemoglobin and the pH dependent binding of serine protease inhibitors for their cognate serine proteases. Mechanistically, this pH dependence arises from a binding induced $pK_a$ change of an ionizable residue(s). Molecular switch functionality is a modulation of function (and as used herein, generally refers to binding) through an environmental trigger (e.g. pH, ion binding, molecule binding) that brings about a shift in the coupled equilibrium. Molecular switch functionality renders binding sensitive to an environmental trigger.

Figure 1:
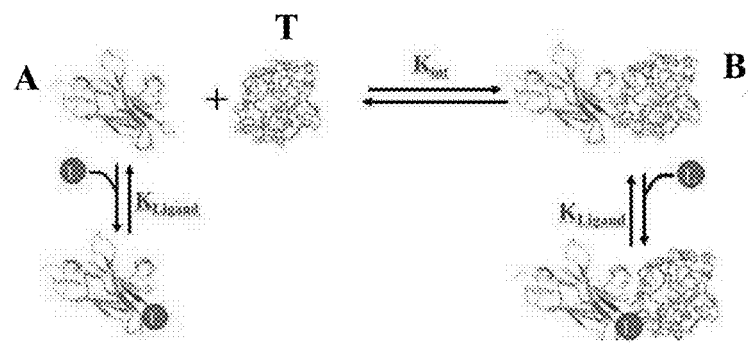
FIG. 1 shows a coupled equilibria scheme where binding of ligand (circle with L) to either the free (A) or complex (B) state of a protein reagent with its target molecule (T) results in a ligand (circle with L) dependent decrease or increase in observed affinity of the reagent for its target molecule.

FIG. 1 shows a coupled equilibria scheme where binding of ligand (encircled L) to either the free (A) or complex (B) state of a protein reagent with its target molecule (T) results in a ligand (encircled L) dependent decrease or increase in affinity of the reagent for its target molecule. In this case the protein reagent is an antibody, Kint, that represents the intrinsic antibody/antigen binding constant, and KLigand is the affinity of the ligand for the antibody or antibody/antigen complex.

In coupled equilibria, cause and effect can of course be reversed, depending on the requirements of the user. For example, if the goal is a protein affinity reagent which releases a ligand, such as a metal ion, then molecular switch functionality can be designed with a hapten or antibody as the environmental trigger for the release of the ligand.

Protein affinity reagents engineered to include molecular switch functionality in the form of multiple ionizable residues introduced into the target binding interface of the protein reagent are disclosed. These protein reagents are designed according to the novel principle that the inclusion of appropriate multiple ionizable residues at appropriate sites in the target binding interface makes the affinity of the protein reagent highly sensitive to environmental triggers without significantly altering affinity in the absence of the trigger.

Alanine scans of protein-protein interfaces have demonstrated that certain residues contribute more than others to the overall binding affinity, the so-called binding "hot spots". These studies have also demonstrated that a large fraction of interface residues are energetically neutral towards the binding affinity. Consequently, many interface side chains likely may be substituted without significantly altering the native binding affinity of a protein affinity reagent. Inclusion of appropriate multiple ionizable residues confers molecular switch functionality. Ionizable residues such as histidine can alter the three dimensional structure of a protein upon protonation or deprotonation.

Figure 3A:
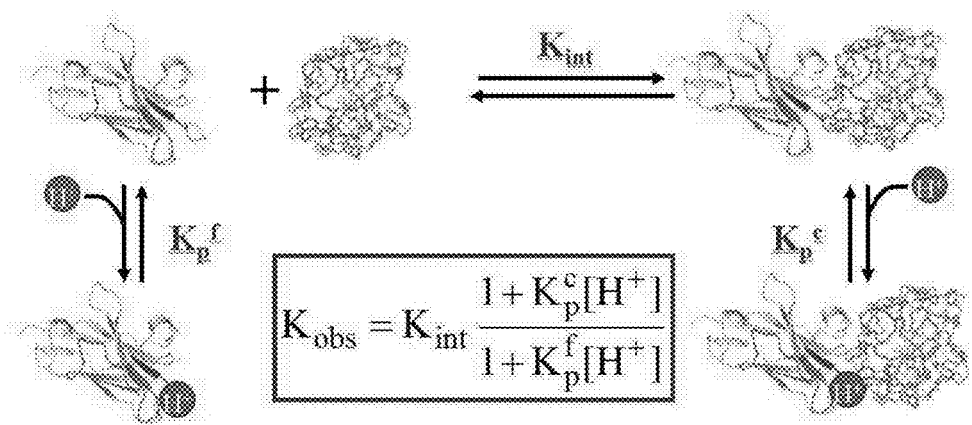
FIG. 3A shows a thermodynamic model wherein a single proton is represented as a circled H.

The ability to introduce pH sensitive binding requires the inserted residue to experience a change in $pK_a$ upon binding (FIG. 3A). Numerical simulation is shown in FIG. 3B.

Figure 3B:
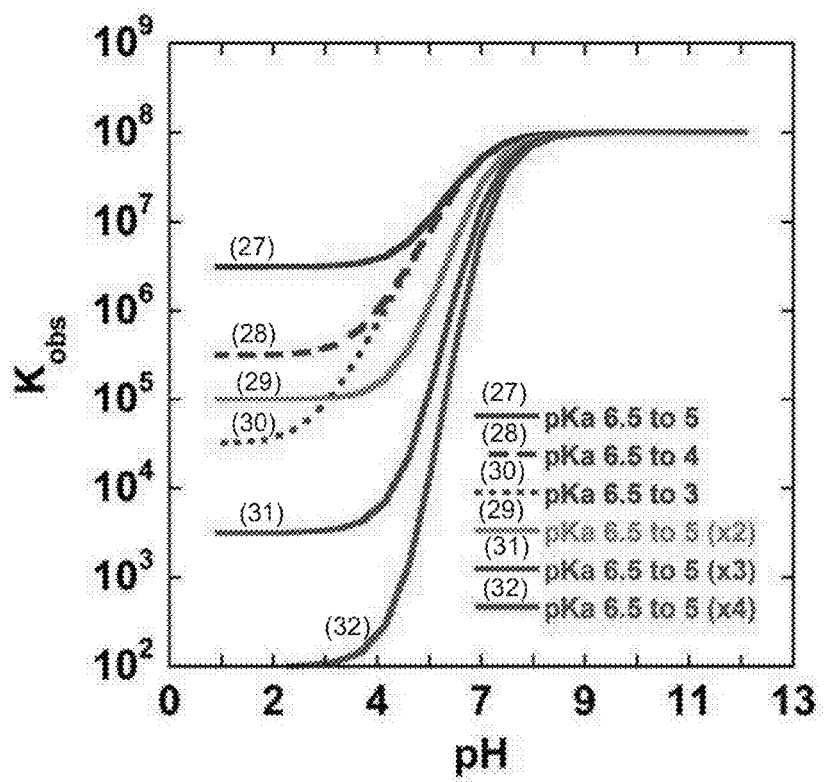
FIG. 3B shows a simulation illustrating the pH dependence of the observed binding constant, $K_{obs}$, which is dependent on both the magnitude of the ionizable residue's $pK_a$ change, as well as the number of ionizable groups undergoing a $pK_a$ change upon binding.
Figure 3C:
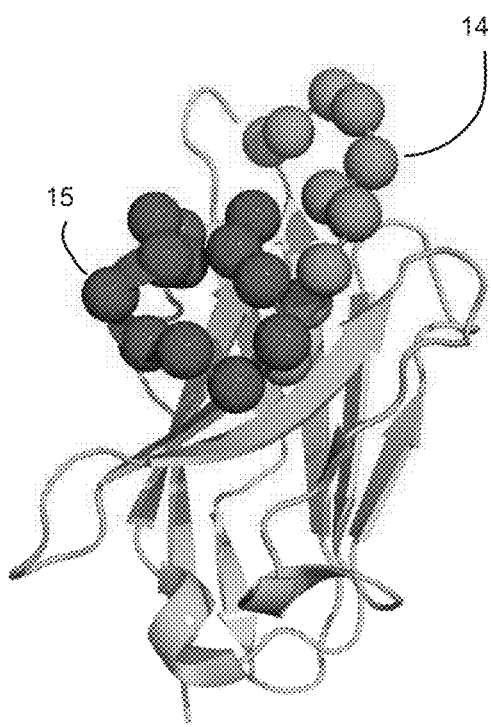
FIG. 3C shows a ribbon representation of the single domain anti-RNase A VHH antibody, with the alpha-carbons of the CDR1 (14); CDR3 (15)

FIG. 3B displays a plot of numerical simulations for a protein interaction exhibiting different extents of linked proton binding. The plot predicts that the extent of $pK_a$ perturbation and, more importantly, the total number of ionizable groups undergoing $pK_a$ changes will significantly impact the degree of pH sensitivity. For example, a single, well placed histidine group that experiences a significant $pK_a$ drop of 3.5 units on binding only exhibits limited pH sensitivity over the pH range of 7-4. The full thermodynamic effect of such linkage is only apparent at very low pH values where other ionization events (such as those involved with protein stability) will likely begin to dominate. On the other hand, when multiple histidines are present, with each experiencing modest 1.5 unit drops in $pK_a$ on binding, a dramatic enhancement of pH sensitivity is observed, where the maximum value of the slope of dlogK/dpH equals the number of ionizable groups involved (i.e., 2, 3, or 4 groups).

In the Examples herein, multiple histidines were introduced into the CDRs of anti-RNase A antibodies. These antibodies exhibit antigen binding affinity comparable to that of wild type antibodies at physiological pH but show approximately a 1,000 fold decrease in affinity as pH is reduced to 5. In contrast, engineered antibodies previously reported show only a 10-fold decrease in observed binding with a one to two unit decrease in pH. Molecular switch functionality can be introduced into many types of antibodies and other protein affinity reagents, using methods described in detail in Examples 2 and 3.

Although pH-dependent binding involves the protonation or deprotonation of one or more ionizable groups upon protein-target binding, ligand binding is yet another biological method of regulating protein binding and stability. The binding of ions and small molecules can be frequently linked to protein binding. One common biological protein-ion interaction involves the use of histidine to bind metals ions, including $Zn^{2+}$, $Co^{2+}$, and $Ni^{2+}$. Histidine side chains can modify the three dimensional structure of a protein upon associating or dissociating from these metals. A histidine-scanning anti-RNase A antibody library, described in Example 2, is useful to select antibody variants having metal sensitive molecular switch functionality. For example, a selected antibody clone, which possessed a molecular switch motif including three histidines, displayed a 1,000 fold decrease in IC(50) values in the presence of a 1 mM mixture of $Zn^{2+}$, $Co^{2+}$, and $Ni^{2+}$, whereas the wild type antibody was insensitive, as shown in FIG. 10A.

Figure 2:
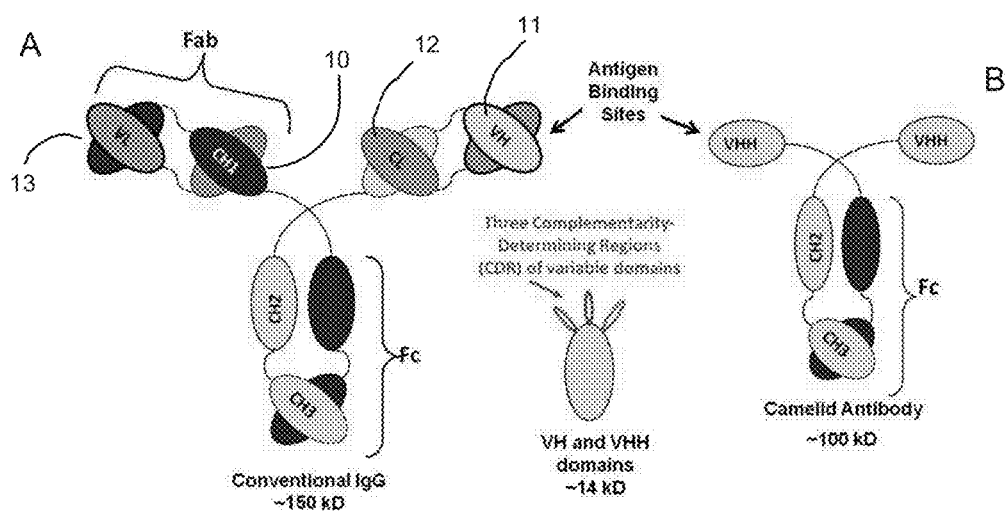
FIG. 2A shows a schematic of a conventional IgG antibody consisting of two heavy (10, 11) and two light (12, 13) chains.
FIG. 2B shows a schematic of unique camelid antibody devoid of light chains and the minimal binding unit of camelid VHH antibodies, which shares close sequence homology to human VH domain.

The pH and metal sensitive antibodies of Examples 1 and 2 are based on a platform of camelid antibodies. Camelid heavy chain only antibodies, found in camelidae such as camels and llamas, are a subset of IgG antibodies lacking light chains, possessing only a single variable domain, termed VHH that binds target molecules (FIG. 2). These minimalist antibodies are preferred as protein affinity reagents because of their small size, ease of recombinant production and the fact that they can possess affinities and specificities for their target protein molecules that rival conventional IgGs. Any class of antibody, specific for any antigen or hapten, whether engineered or selected from a biologically or synthetically based library of monoclonal antibodies is suitable.

The incorporation of histidines as the ionizable residues in the example antibodies has proven most favorable for the creation of pH and metal sensitive switches for antibody affinity. Other ionizable residues such as arginine, lysine, aspartic acid, and glutamic acid, also can be useful in other types of protein reagents, pH responsive switches, or in other switches.

Preferably, a plurality of ionizable amino acids are introduced, most preferably histidine residues. Arginine, lysine, aspartic acid, and glutamic acid residues can additionally or alternatively be introduced.

Existing methods of simulation and prediction through molecular modeling are inadequate to meet the demands of designing such multi-residue molecular switch motifs. The effects of the protein microenvironment upon the binding constants of multiple ionizable residues, the changes in those constants by protein microenvironmental alteration during binding of a trigger ligand or target protein, and the effects of the ionizable residues on target binding in the absence of the trigger, cannot be predicted with sufficient accuracy. Disclosed herein is a different, combinatorial approach, wherein protein affinity reagents are selected on the basis of molecular switch functionality. The selected protein affinity reagents are immediately useful as reagents. For example, the binding of complex mixtures of antibodies, with molecular switch functionalities sensitive to different pH levels, can be controlled through slight changes in pH. The selected protein affinity reagents are also useful as tools for the further rational development of molecular switches, as the motifs that confer their molecular switch functionality can be analyzed retrospectively.

Therefore, a combinatorial ionizable residue protein scanning expression display library of variants of a wild type protein affinity reagent is provided wherein at least one amino acid residue across a target binding interface of the protein affinity reagent is encoded at least once as an ionizable amino acid residue and at least once as the wild type residue. The only information required for the making and use of this library is the amino acid sequence of the target binding interface. A method of creating an ionizable residue-scanning expression display library of variants of a wild type protein affinity reagent wherein at least one amino acid residue across a target binding interface of the protein affinity reagent is encoded at least once as an ionizable amino acid residue and at least once as the wild type residue, includes (a) determining the amino acid sequence of the target binding interface of the wild type protein affinity reagent, (b) creating a nucleic acid library (e.g DNA or mRNA) wherein at least one residue of the target binding interface is encoded at least once as an ionizable amino acid residue and at least once as the wild type residue, and (c) cloning the nucleic acid library into an expression display vector system.

Synthetic libraries are preferred to natural libraries for use in the present invention, because they can possess far greater structural and chemical diversity than natural antibody libraries, whose diversity is limited to the organism's immune system. Synthetic libraries can also be focused to complement structural/chemical properties of the target. Methods are disclosed in Examples 1 and 2 for the making and use of M13 phage libraries of degenerate oligonucleotides based on the target binding interface of an antibody to RNase A. These methods are easily adapted to any protein affinity reagent.

A dual selection method of screening the large number of diverse clones included in such libraries, which runs to several million in the examples to be discussed, and theoretically ranges up to $10^{10}$, is disclosed. These dual selection methods enable a user to efficiently identify library constructs which make the affinity of a protein reagent highly sensitive to environmental triggers such as specific pH values, but which retain normal levels of affinity in the absence of the trigger.

Briefly, the target molecule is linked to a substrate, with biotin linkage of the target to streptavidin-coated magnetic beads being preferred. An expression display library of the type discussed above, preferably an M13 phage library, is incubated with the target-linked beads in the absence of an environmental trigger, e.g. at physiological pH when pH dependent switch functionality is desired. Each clone in the library displays a variant of the protein affinity reagent or a region thereof. The beads are pulled down, and the phage that are bound to the beads constitute the target binding population for the first round of selection.

To select variants which show decreased binding in the presence of an environmental trigger, the target binding population is incubated in the presence of the trigger, e.g. at pH 4.0. Phage eluting in the presence of the trigger constitute the modifiable target binding subpopulation for the first round of selection, as their binding is modified by the trigger.

Preferably, additional rounds of selection are performed, with the selection becoming more stringent at each round. For example, for the selection of pH responsive molecular switch functionality, the beads bear a lower density of target at each round, and the pH moves progressively closer to physiological pH, for example reaching pH 5.5 at the final round.

The modifiable target binding subpopulation from the final round of selection is then amplified and cloned, and cloned variants with the desired molecular switch functionality are identified. Identification can be by means of comparison of selected and wild type variants in competitive ELISAs in the presence and absence of the environmental trigger, by the determination of target binding constants of selected and wild type variants by isothermal titration calorimetry (ITC), or by any other suitable measure known in the art.

To select variant protein affinity reagents whose target binding affinity is increased in the presence of the environmental trigger, the selection process is modified. The concentration of target is still decreased with each round of selection, to increase binding stringency, but the environmental trigger is present at all rounds of selection. Preferably, the strength of the trigger is also decreased with each round. The modifiable target binding subpopulation therefore constitutes the variants that show enhanced target binding in the presence of a relatively subtle environmental trigger. This subpopulation is eluted by disrupting the covalent bond between the binding target and the beads.

Phage display libraries such as M13 are preferred because as they possesses a relatively large upper limit on library size ($10^{10}$ unique members) and allow complete control of experimental conditions, including temperature, buffer, and elution method to allow fine tuning of selection. Libraries described herein can also be created in other phage systems, or in any system which links protein phenotype, such as antigen binding, with the genotype of the gene encoding the protein. These systems can include display on yeast, microbial cell walls or inner membranes, or retrovirus, and they can also include ribosome and mRNA display (Hogenboom 2006, Fellouse et al. 2007).

Selection of clones of the library can be by any means of panning known in the art, for example with the binding target attached to a planar substrate, or with the target attached to particles in a column.

Thus, a method for introducing molecular switch functionality into a wild type protein affinity reagent that binds a target molecule via a target binding interface, includes the steps of providing an ionizable residue-scanning expression display library of variants of the protein affinity reagent wherein at least one amino acid residue across the target binding interface is encoded at least once as an ionizable amino acid residue and at least once as a wild type residue, selecting at least one protein affinity reagent variant on the basis of its binding to the target molecule in the absence of an environmental trigger, defining the at least one protein affinity reagent variant binding to the target molecule in the absence of an environmental trigger as a target binding population, selecting from the target binding population at least one member that exhibits modified binding to the target protein in the presence of the environmental trigger, defining the at least one member of the target binding population that exhibits modified binding to the target molecule in the presence of the environmental trigger as a modifiable target binding subpopulation, and identifying at least one member of the modifiable target binding subpopulation of protein affinity reagents as a protein affinity reagent with molecular switch functionality sensitive to the environmental trigger.

Protein affinity reagents possessing molecular switch functionality are produced by the above method.

Together, the combinatorial protein binding residue-scanning library and the dual selection method of screening the library constitute a combinatorial library-based ionizable residue-scanning approach. A major advantage of this approach over the prior art is that it requires no detailed structural knowledge of the antibody or other protein of interest, only knowledge of the interface residues. For example, the only structural information utilized in the development of the anti-RNase A VHH histidine scanning library of the present invention was the knowledge that the CDR1 and CDR3 of the VHH are involved in binding the RNase A target, and the amino acid sequence of those regions. Histidines were broadly sampled throughout CDR1 and CDR3, including both surface exposed and scaffolding residues.

The combinatorial approach can be easily modified to explore additional interface or scaffolding residues or leave specific residues unchanged. In fact, the method is completely scalable up to larger interfaces (e.g., conventional antibodies with interfaces possessing both heavy (VH) and light (VL) variable domains) where as many as 30-35 residues can be sampled by combining modern phage (Sidhu and Weiss, 2004) display or mRNA display technologies (Lipovsek and Pluckthun 2004), using trinucleotide (trimer) phosphoramidite based degenerate oligonucleotides (Fellouse et al. 2007).

When the combinatorial library-based proton binding residuescanning approach was used to create a library wherein all 22 positions at the RNase A-VHH binding interface sampled histidine, antibodies were produced that possessed near wild type affinity for RNase A, and an approximately 1,000 fold decrease in binding over a pH change of approximately 2 units. Antibodies were also produced that showed similar sensitivity to the presence of 1 mM metal ions. The combinatorial library based scanning approach therefore produces antibodies with molecular switch functionalities that could not be generated by conventional methods of molecular design.

Although the Examples describe the generation of antibodies with molecular switch motifs sensitive to pH and metal ions, the use of the methods and compositions are readily extended to other protein reagents, including those that bind small molecules, DNA, and carbohydrate, and to other triggers. All that is required is identification of the amino acid residues of the reagent that are critical to target binding.

After protein affinity reagents with molecular switch functionality have been identified, they can be employed in many ways. For example, the ionizable residue-scanning expression library can be one wherein the whole protein affinity reagent is expressed. In that case, the gene for the protein affinity reagent can be used directly, while still integrated with the vector. Alternatively, the reagent can be cloned into an expression vector such as pET-21a plasmid, produced in competent cells such as BL21(DE3), and purified as described in the Examples. The protein affinity reagents can be used in any type of biological, medical, or industrial purification or analysis procedure known in the art, or they can be characterized as guides for the further development of molecular switches. After being characterized, the motifs can be incorporated into protein affinity reagents by methods well known in the art. For example, the portion of the protein binding interface containing the molecular switch motif, such as the CDRs of an antibody, can be grafted onto a suitable protein platform.

The protein affinity reagents are useful in a variety of affinity purification and controlled-release application. They can be used, for example, in antibody affinity columns of which upon which target antigens or haptens can be bound and released according to the pH values or metal ion concentrations of the column buffers. Antibody columns elutable by changes in pH or ionic strength levels are known in the art, but elution generally requires strongly acidic or basic buffers. Such buffers can cause irreversible damage to the target molecule, and also to the antibody, rendering a costly column unfit for re-use. Protein affinity reagents described herein allow the performance of both binding and elution of a target at pH or ion levels that are well within physiological levels. The protein affinity reagents and methods are also useful in the design of controlled-release delivery platforms. A protein affinity reagent can include molecular switch functionality that favors the binding of a pharmaceutical at a specified level of pH or metal ions, but favors the release of that pharmaceutical in the presence of a different level of pH or metal ions, a level that is the environmental trigger for release. Thus, a method is provided for controlling the binding and release of a target molecule by a protein affinity reagent by means of an environmental trigger, including the steps of providing a protein affinity reagent including a molecular switch motif rendering the affinity of the protein affinity reagent sensitive to the environmental trigger, providing the target molecule, incubating the protein affinity reagent with the target molecule, and regulating the presence of the environmental trigger.

As advances are made in the design and incorporation of molecular switch functionality into protein affinity reagents, it is important to expand the range of target molecules to which these reagents can be applied. Haptens include many important pharmaceuticals and environmental toxins. Specific and sensitive hapten-binding reagents reagents can be of great use in diagnostics, environmental testing, therapeutics, and industrial processes. For example, an antibody that binds an anti-cancer drug with high affinity, but that releases the drug at the low pH characteristic of tumor microenvironments, can be a most effective drug delivery system.

Traditionally, anti-hapten antibodies are generated by coupling the hapten to a larger protein and eliciting an immune response against the haptenprotein conjugate. While such antibodies are readily developed, they often display low affinity and specificity for the hapten. This is partially explained by a failure of full antibody recognition of the entire due to steric hindrance from the protein conjugation. Recent advances in the development of antibodies through in vitro selection can allow novel mechanisms of recognition that have previously not been possible with conventional antibody approaches.

Coupling of two VHH antibodies can be used to thermodynamically drive hapten recognition. While hapten/antibody complexes typically follow a 1:1 stoichiometry, it was found that complexes of VHH domains and caffeine can form, with a unique 2:1 VHH:caffeine stoichiometry, with each VHH domain recognizing a different site on the hapten. Essentially, the two VHH domains form a sandwich around the hapten molecule (FIG. 14). The sandwich can bind a hapten with dramatically greater affinity than either VHH domain alone, or a conventional antibody containing two identical variable domains.

This finding has led to a new in vitro selection method for generating anti-hapten antibodies with greater affinity than those in the prior art. The method, described in detail in Example 3, is performed by (a) providing a library of VHH domains, (b) starting with an existing 1:1 anti-hapten antibody complex, selecting a first VHH domain that specifically binds a first site on the hapten, (c) forming a first VHH-hapten complex including the first VHH domain and the hapten, (d) capturing the first VHH-hapten complex, (e) selecting a second VHH domain which specifically binds the first VHH-hapten complex, (f) forming a second VHH-hapten complex including the first VHH-hapten complex and the second VHH domain, and (g) identifying the combination of the first VHH domain and the second VHH domain as a protein affinity reagent specific for the hapten. The combination of first and second VHH domains can additionally fused to form a single two-chain unit. While camelid VHH domains are preferred, any type of single chain antibody is potentially suitable. Molecular switch functionality can of course be introduced by the methods discussed herein and described in detail in Examples 1 and 2.

The methods and products disclosed herein can be used in controlling protein target interactions in vitro, within the body, or in any biological system, wherein "controlling" includes either decreasing or increasing the strength of a protein-target interaction. Examples are provided for the purpose of illustration only, and are not intended to be limiting unless otherwise specified.

Definitions

Abbreviations: ITC: isothermal titration calorimetry, VHH-wt: wild-type anti-RNase A VHH, VHH-10: pH clone #10, VHH-24: pH clone #24, ASA: solvent accessible surface area, ΔASA: Change in solvent accessible surface area.

Affinity: Force that impels certain atoms to bind or unite with certain others to form complexes or compounds.

Combinatorial library: Every possible combination of an ionizable amino acid e.g. histidine and a wild type residue is encoded; may be nucleic acids (DNA, mRNA) or proteins.

Ionizable residue-scanning protein library, (expression display library): Library which samples ionizable residues throughout a protein interface; typically consists of sampling ionizable residues throughout an existing protein interface; not limited to an existing protein interface as ionizable residues could be sampled in a naïve, synthetic library.

Molecular Switch Functionality: The ability to respond to a specific environmental trigger with an alteration in target binding affinity.

Molecular switch motif: Refers to any pattern of amino acids which, when introduced into a protein affinity reagent, confers molecular switch functionality to that reagent, or enhances its existing molecular switch functionality. The pattern of amino acids can include a sequence of amino acids, a spatial arrangement of amino acids, or both.

Specificity: Relation of antigen to an antibody.

Target binding interface: Refers to both the surface exposed and scaffolding residues of a region of a protein affinity reagent that interacts with a target molecule.

Wild-type: Refers to the structure of an existing protein affinity reagent to be controlled; usually refers to the primary amino acid sequence.

EXAMPLE 1

Design and Engineering of pH Dependent Molecular Switch Functionality into an Antibody There is growing interest in the development of protein switches; one such example is pH dependent protein-protein interactions. A novel, synthetic, combinatorial library was developed to sample histidines throughout a model single domain antibody interface. This approach is both rapid and robust, and is capable of producing numerous highly pH-sensitive antibody variants that would otherwise, not likely be generated using traditional design methods.

Chemical Basis for pH-dependent Binding

Mechanistically, the engineering of pH sensitive binding requires that the inserted residue (e.g., histidine) or functional group undergo a change in $pK_a$ on binding (FIG. 3A). This change in $pK_a$ value stems from the ionizable group's sensitivity to a change in microenvironments (e.g., those present in bound and unbound states or folded and unfolded states). For example, protein stability studies by Garcia-Moreno and coworkers have revealed a surprising range of shifts in $pK_a$ values for ionizable groups that become buried in dehydrated environments (Isom et al. 2008, Isom et al. 2011, Isom et al. 2010) Perhaps most importantly, their work reveals that ionizable groups can tolerate seemingly unexpected environments, which may highlight their use in pH-dependent biological events.

Although each of the examples of engineered pH-dependent binding, discussed above, did indeed introduce pH sensitivity, the results do not relate control of binding by pH considering what is thermodynamically possible. To illustrate this point, FIG. 3B displays a plot of simulated binding data for a protein interaction exhibiting different extents of linked proton binding. The extent of $pK_a$ perturbation and, more importantly, the total number of ionizable groups undergoing $pK_a$ changes, will significantly impact the degree of pH sensitivity. For example, a single, well placed histidine group that experiences a significant $pK_a$ drop of 3.5 units on binding only exhibits limited pH sensitivity over the pH range of 7-4. The full thermodynamic effect of such linkage is only apparent at very low pH values where other ionization events (such as those involved with protein stability) will likely begin to dominate. On the other hand, when multiple histidines are present, with each experiencing modest 1.5 unit drops in $pK_a$ on binding, a dramatic enhancement of pH sensitivity is observed, where the maximum value of the slope of dlogK/dpH equals the number of ionizable groups involved (i.e., 2, 3, or 4 groups). In practice, engineering pH-sensitive binding through the introduction of one, two, or more ionizable groups into a protein interface is a difficult task as simple correlations between a histidine's $pK_a$ and its structural environment are not obvious. This is a problem that cannot be solved through prediction or simulation as one cannot predict shifts in $pK_a$ with sufficient accuracy. Furthermore, the inserted ionizable residue must not only undergo a $pK_a$ perturbation on binding, but also must not dramatically interfere with high-affinity binding at the permissive pH.

Previous approaches to insert histidine residues within a protein interface were often guided by structural knowledge of the protein complex. These approaches have limitations, as only a small subset of the structural and energetic space is ultimately sampled. These techniques also tend to be time and cost intensive. Finally, although knowledge of the protein complex structure may certainly be useful toward engineering pH sensitivity, many, if not most, antibody affinity reagents are limited to knowledge of only the amino acid sequence.

Design and Selection of pH-dependent Linkage

Highly pH-sensitive binding was engineered into a model antibody/antigen system, anti-RNase A VHH/RNase A, which was selected due to its high affinity ($K_d$~20 nM) and lack of appreciable pH dependence to the binding affinity (down to at least pH 3.5). To introduce significant pH dependence within the anti-RNase A VHH interface, a novel, combinatorial scanning phage display strategy was developed. In contrast to traditional interface alanine-scans or shotgun alanine scans, where the loss or retention of function (e.g., binding, enzymatic activity) on side chain removal is revealed, a histidine interface scan probes locations that introduce new function (i.e., proton binding sites). This approach exploits the frequently observed plastic nature of protein interfaces, whereby a large percentage of interface residues can tolerate substitution without dramatic loss in binding affinity. Using oligonucleotide directed mutagenesis strategies (Sidhu and Weiss, 2004), an M13-phage library of degenerate oligonucleotides was generated so that each residue position within the anti-RNase A VHH binding interface, which includes a total of 22 residues, was allowed to sample both histidine and the original wild-type residue, as shown in FIG. 3C. The resulting library (with a theoretical diversity of $10^{10}$) simultaneously ensures complete histidine saturation (i.e., every possible combination of histidine at each position is sampled within the interface), while allowing retention of wild-type residues that are necessary for high-affinity binding at physiological pH.

Phage selection included two key steps for dual function screening: binding and elution. Initially, RNase A-binding library members were subjected to solution capture at physiological pH (7.4) using biotinylated RNase A and streptavidin-coated magnetic beads. Phage particles retained on the magnetic beads were subjected to several wash steps to remove low-affinity variants. The second step involved phage elution where the pH-sensitive variants were released using moderately acidic conditions (pH 4.0-5.5).

These clones were then reamplified and subjected to additional rounds of pH 7.4 binding and acidic pH elution. After three rounds of selection, immunoassays were used to screen for clones possessing pH-dependent binding. These assays demonstrated that, unlike wild-type anti-RNase A VHH, complete loss of binding was observed for all 26 clones tested when the pH was lowered from pH 7.4 to 4.0. The location and extent of histidine incorporation was determined through DNA sequencing. The sequences of the resulting 26 unique clones (of 48 sequenced) are displayed in FIG. 4A.

Figure 4:
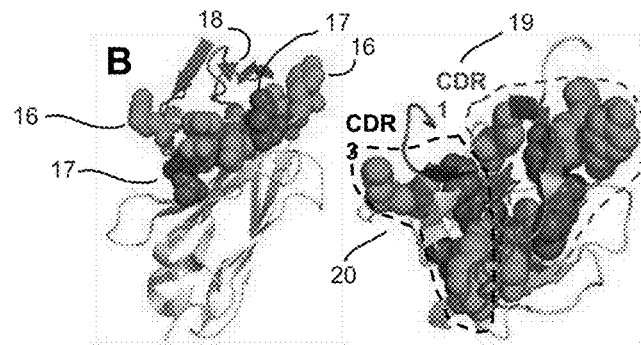
FIG. 4A shows amino acid sequences of the interface CDRs of pH sensitive third round output VHH variants (FIG. 4A discloses the "CDR1" sequences as SEQ ID NOS 7-30, 17, and 31-32, respectively, in order of appearance and the "CDR3" sequences as SEQ ID NOS 33-34, 33-34, 33-34, 34, 34-40, 33-34, 34, 34, 34, 33, 39-40, 33, 41, 35, 42, and 35, respectively, in order of appearance)
FIG. 4B shows side (left) and top (right) views of the anti-RNase A VHH binding interface, with anti-RNase A VHH residues that tolerate incorporation of histidine displayed in (16) and residues that are invariant (17), and with the RNase A binding interface displayed as a cartoon ribbon (18); the CDR1 surface-(19) is represented as a dotted line, and the CDR3 surface as a black dotted line (20)
FIGS. 4C and 4D show top (C) and side views (D) of the VHH interface side chain residues by histidine hot-spot incorporation frequency, with a provided in the legend and RNase A represented by white sticks.
Figure 4:
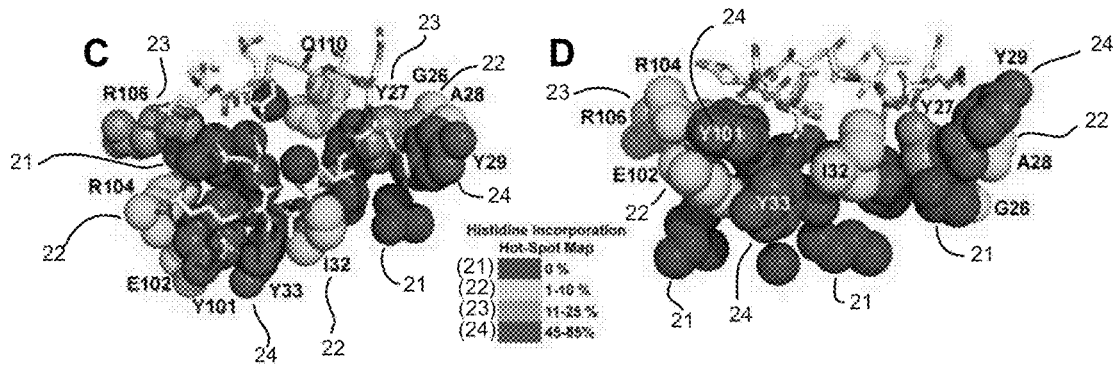

Overall, histidines are well tolerated in the interface (up to 5 new histidines), and reside in both loops, CDR1 and CDR3 (FIG. 4B). Residues that are known to be invariant across VHH sequences are maintained. Of the 22 residue positions sampled in the His/Wt library, 10 different positions within the CDR1 and CDR3 binding loops tolerated histidine incorporation. This relates to 45% incorporation coverage, suggesting histidines are very well tolerated within the small VHH interface. Spatially, histidines are present in both interface loops, CDR1 and CDR3, with a slight preference for CDR1. FIGS. 4C and 4D present a histidine insertion "hot-spot" map of the VHH interface. There is a clear preference for histidine substitutions within the interface periphery. Conversely, interface residues that do not tolerate histidine substitutions (i.e., the cold-spots) are located centrally, some of which protrude into the VHH interior, where they participate in hydrophobic intramolecular interactions. The number of simultaneous histidine incorporations is perhaps the most striking observation. VHH variants possessed a minimum of two and up to a maximum of five histidines within the binding interface. Notably, approximately one third of the unique clones had "paired" histidines, where two histidines are located adjacent to each other in sequence or space. Thus, one family of molecular switch motifs for the pH dependence of RNase A affinity have been found to be characterized by multiple histidine substitutions, often in pairs, at the periphery of the target binding interface.

Figure 5A:
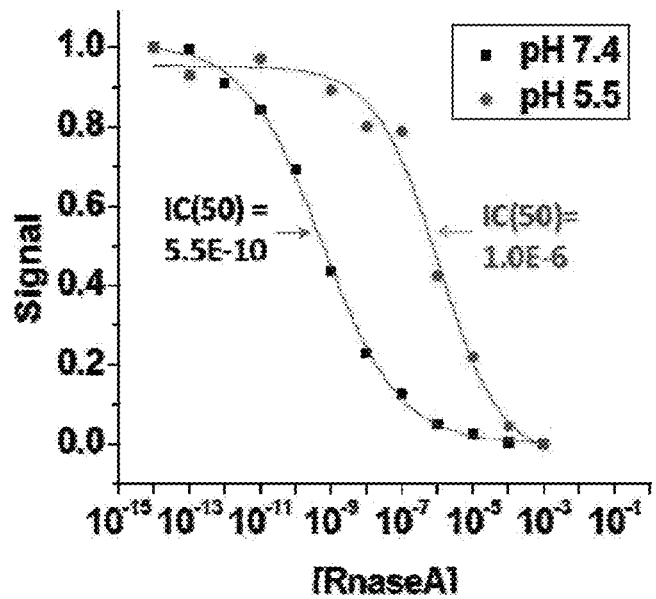
FIG. 5A shows the results of competitive ELISA of representative His-scanned-VHH clone 6.

Competitive ELISA experiments were run to determine the relative effect of pH on binding between wild-type and three representative clones. As no signal was observed at the selection pH 4.0, suggestive of the introduction of dramatic pH dependence, experiments were run at pH 7.4 and pH 5.5 (FIG. 5A). In general, wild-type affinity is maintained at physiological pH, and a significant (~1000-fold) decrease in binding is observed (when detectable) upon a pH decrease of ~2 units. Taken together, these results support the methodology and show that extremely sensitive pH dependence can be introduced, which includes multiple histidines experiencing perturbed $pK_a$ values upon binding.

Detailed Analysis of the pH Dependence

A detailed analysis of the observed binding constant, $K_{obs}$, was performed to address the central question whether significant pH dependence can be introduced with multiple, well-placed histidine residues. Isothermal titration calorimetry (ITC), which allows the determination of binding constants, $K_b$, with high accuracy, was used to measure the protein-protein binding constant over a range of pH values.

Two prototypical VHH variants were selected to determine the binding properties over a range of pH values. Table 1 is a table of the binding thermodynamics as a function of pH. This included VHH#10, which is the "consensus clone" possessing the three "hot-spot" histidine substitution sites, Y29, Y33, and Y101 and VHH#24, which possessed five interface histidines (FIG. 4A).

Figure 5B:
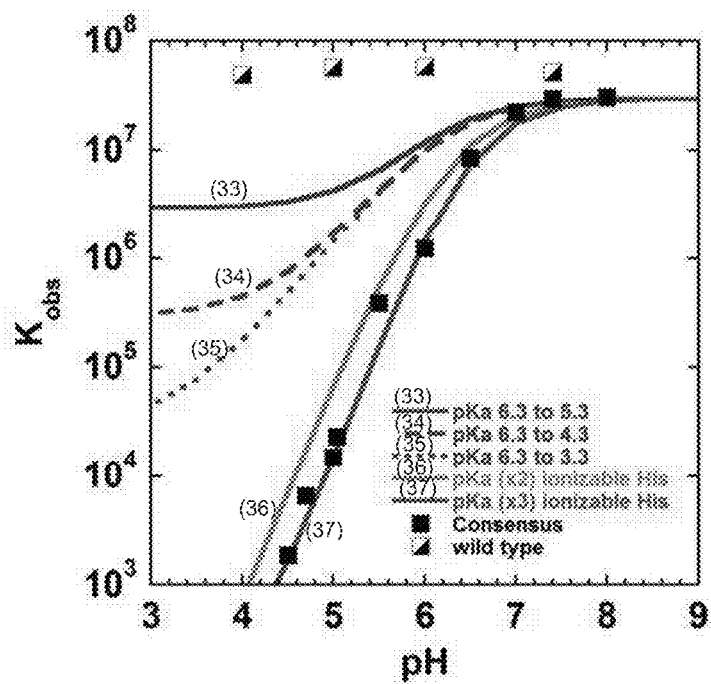
FIGS. 5B and 5C, show the pH dependence of the observed binding constant, $K_{obs}$, for the consensus ■VHH#10 (B) (33-35) and VHH#24 (C) (38-40) variants; for reference, the wild-type VHH/RNase A binding data are presented in "half-solid squares", as well as simulated curves for a single ionizable group undergoing a range of $pK_a$ changes (36-37; 41-42); stimulated curves for two and three histidines undergoing $pK_a$ changes are also presented.
Figure 5C:
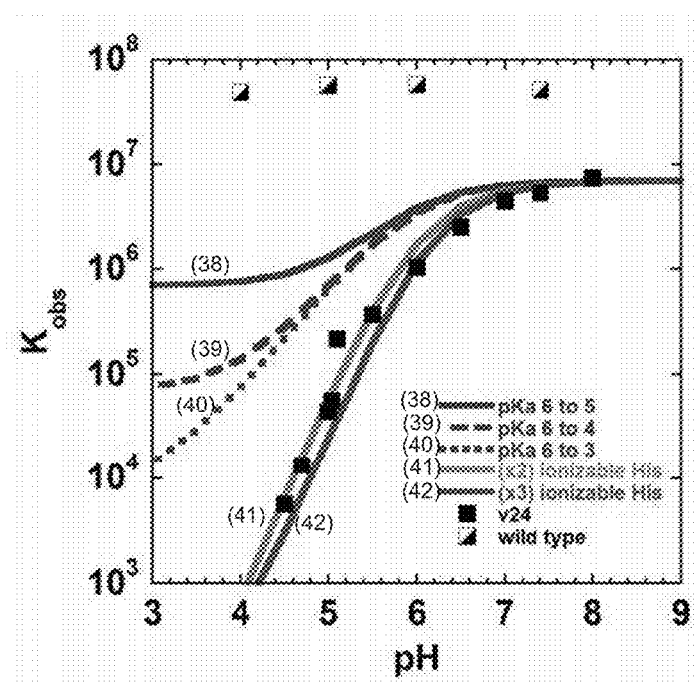

FIGS. 5B and 5C display the binding constant profiles from pH 4.5 to 8.0. At the permissive pH, 7.4, both variants VHH#10 and VHH#24, possessed binding affinities within twofold and fivefold of the wild-type value, respectively. This corresponds to dissociation constants, Kd, of 35 nM (VHH#10) and 91 nM (VHH#24). On decreasing the pH, the observed binding constants decreased by ~104 over a range of ~2 pH units. Determination of binding constants below pH 4.5 was not feasible, due to low binding signal; however, the pH profile displays no indication of a lower plateau near pH 4.5, showing that the binding constant would continue to decline as pH is decreased further. This trend would correspond to a binding constant that is no greater than a value of 100 ($K_d$=10 mM), at pH 4.0.

To rule out simple pH-based unfolding as the cause of the decrease in binding affinity, VHH#10, VHH#24, and VHH-wt were analyzed by far-UV circular dichroism (FIGS. 6A to 6C). Overall, both pH-sensitive VHH variants exhibit no major change in structure down to pH 4.0, which is below the lowest pH performed using ITC (pH 4.5). The pH profiles of both variants are quite similar to that of the parent VHHwt.

In addition, thermal denaturation experiments were performed using circular dichroism (CD). At physiological pH, the wild-type, VHH#10, and VHH#24 variants all possessed comparable Tm values, 68.0±0.3, 64.3±0.1, and 66.4±0.1° C., respectively, as shown in FIG. 7. When the pH was lowered to pH 4.0, the $T_m$ values were 61.2±0.2, 53.4±0.2, and 49.7±0.2° C., for the wild-type, VHH#10, and VHH#24 variants, respectively (FIG. 7). Despite a larger drop in Tm (relative to VHH-wt) when going from pH 7.4 to 4.0, both pH-sensitive VHH variants remained 100% folded up to ~45° C. at pH 4.0, well above the temperature used in binding analysis (10-25° C.).

When multiple ionizable groups undergo $pK_a$ changes on binding, detailed information of individual $pK_a$ values (or protonation thermodynamics) cannot be easily determined from simply fitting proton linkage models to $K_{obs}$ versus pH data, due to a high correlation between the protonation thermodynamic parameters (e.g., $pK_a$, $\Delta H_{protonation}$, etc.). Despite this limitation, manual fits are capable of revealing insight into the extent of histidine participation. The simulated fits are presented in FIGS. 5B and 5C. Data were analyzed using models that included one, two, or three, ionizable histidines. A simple assumption was made that each protonation equilibrium behaves independently. Although neither a single or double histidine model adequately fit the VHH#10 data, a double histidine model can represent the VHH#24 data rather well; however, a significant $pK_a$ drop of at least four units was required for each histidine. On the other hand, a three histidine model matched the observed data using moderate $\Delta pK_a$ values (within a range of 0.5-3).

By including a larger than necessary number of $pK_a$ parameters, the binding data for both variants, VHH#10 and VHH#24, are best fit with at least three contributing histidine residues. Simple analysis of dlog $K_b$/dpH at low pH also shows the slope reaches a value of 3.0, which is consistent with the simulated fits and that at least three histidines are present in both interfaces. Finally, an estimate of the number of protons released on forming the VHH/RNase A complex, due to a drop in histidine $pK_a$ values, may be examined by determining the slope of a linear fit to a plot of the observed enthalpy versus buffer ionization enthalpy as shown in FIG. 8. The VHH#10-RNase A binding event at pH 5.0 (10° C.) possessed 1.78±0.03 protons released on complex formation. Consequently, this analysis also indicates that multiple histidine groups must be responsible for the observed pH-dependent binding.

Structural Analysis of the pH-dependent Variant VHH#24

Figures 5D, 5E:
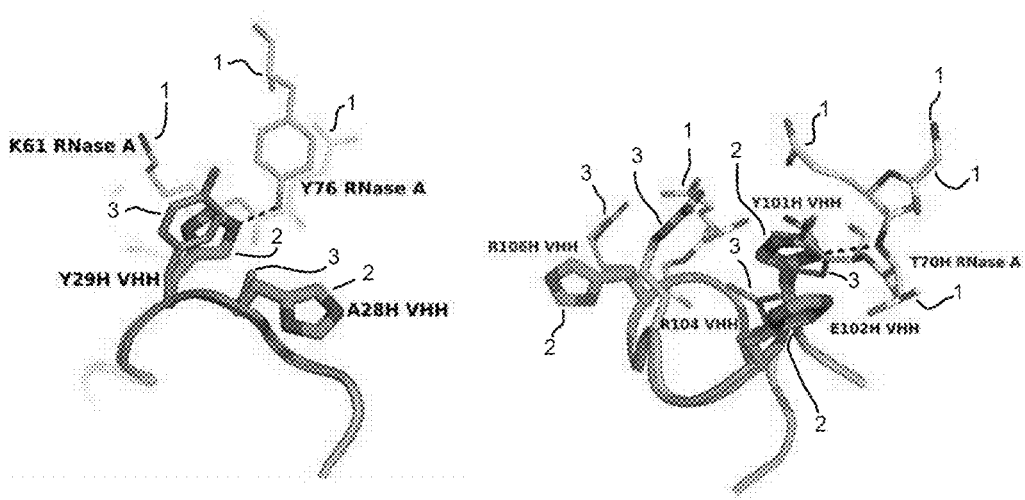
FIGS. 5D, and 5E show structural overlays of the interface loops CDR1 and CDR3, respectively, from the VHH-wt

To understand the structural consequences of introducing a large number of histidines within the VHH interface, the X-ray structure of the VHH#24/RNase A complex was determined. Despite the introduction of five interface histidines (CDR1 residues: A28H and Y29H and CDR3 residues: Y101H, E102H, and R106H), no major structural changes are observed when compared to the original wt-VHH/RNase A complex beyond slight adjustments in side chain conformations, as seen in FIGS. 5D and 5E. All five histidine substitutions are positioned in the interface periphery. Overall, VHH#24, buries slightly less surface area (540 Å° 2) versus VHH-wt (600 Å° 2), which is almost entirely due to loss of contact area from the R106H substitution.

With five potential histidines that may contribute to the observed pH sensitivity, straight-forward structural interpretations of VHH#24's pH-sensitive binding are not possible; however, the VHH#24/RNase A structure provides a model to make several predictions. In general, perturbations of an ionizable group's $pK_a$ value on protein-protein complex formation originate from changes in the residue's microenvironment. In view of this, the structural data reveals two of the five histidine residues bury significant side chain surface area in the VHH#24 complex including Y29H and Y101H, which bury 82 and 61 Å$^2$ of solvent accessible surface area ($\Delta$ASA) on forming the VHH#24/RNase A complex, respectively. As a comparison, the corresponding wild-type residue side chains bury 65 and 64 Å$^2$, respectively. Both histidine side chains make hydrogen bonds with RNase A residues. NE of Y29H forms a hydrogen bond with the side chain of Y77 from RNase A (FIG. 5D), while NE of Y101H forms a hydrogen bond with the main chain of T70 from RNase A (FIG. 5E). Perhaps most relevant, both Y29H and Y101H possess a side chain nitrogen(s) that buries significant surface area. Y29H buries 13 and 29 Å$^2$ for N$\sigma$ and N$\epsilon$ atoms, respectively, while Y101H's N$\sigma$ buries 22 Å$^2$.

In addition to surface area burial, neighboring residues may also influence $pK_a$ values. For instance, both Y29H and Y101H substitutions possess adjacent histidine groups, A28H and E102H, respectively, shown in FIGS. 5D and 5E, that may play a contributing role. The "dual-histidines" are observed to be in close proximity within the VHH#24/RNase A complex, which may result in reduced $pK_a$ values. Of course, the dual histidine environment would need to be different between the free and bound states for them to contribute toward pHdependent binding. Such paired histidine groupings are observed in several of the sequenced variants (FIG. 4A), which shows they can be involved in the pH-dependent binding mechanism. The Y101H/E102H "stacking" observed in the VHH#24 complex (FIG. 5E) is particularly interesting. Although E102H does not exhibit a change in ASA based on a simple rigid-body model of the complex, it is likely to be more exposed in the unbound state and therefore buries intramolecular surface in the bound state, which could influence (drop) E102H's $pK_a$ value. The VHH#24/RNase A structure reveals both Y29H and Y101H groups are also in the vicinity of residues likely to be positively charged. K61 of RNase A is within close proximity to Y29H (FIG. 5D) and R104 of VHH is near Y101H. The positively charged environment may also influence (reduce) pKa values of the histidines in the bound state. The remaining histidine, R106H, does not appear to make appreciable contact with RNase A and is not predicted to play a role in VHH#24's pH-dependent binding (FIG. 5E). Overall, the crystal structure reveals at least two histidines clearly experience new environments on formation of the protein-protein complex with likely contributions from at least another histidine (e.g., E102H). This evaluation is in agreement with the pH dependence data, which suggested contributions from as few as two or three histidines for VHH#24.

Although previous efforts to engineer pH sensitive protein-protein interactions have resulted in pH-dependent binding, these efforts are often at the expense of high-affinity binding at the permissive pH. Typically, this limited pH sensitivity originates from the introduction of only a single ionizable group which is not capable of introducing a large enough change in $\Delta$G to drive a pH sensitive molecular switch. Such a switch, which must undergo a significant change in binding affinity over a short range in pH, can only be generated through the insertion of multiple ionizable groups that undergo a change in $pK_a$ on binding. In fact, the thermodynamic principles which govern a pH-binding switch are analogous to those which drive acid-induced protein unfolding, where multiple ionizable groups contribute to the loss of a protein's stability. Consequently, the generation of a pH switch (whether binding or folding) requires an intimate balance of pH-dependent and pH-independent contributions. Here, a combinatorial histidine/wild-type library was developed to reveal antibodies which possessed this balance of pH dependent and pH-independent terms. This combinatorial approach produced numerous, unique antibodies with highly pH-sensitive binding through the introduction of multiple interface histidine residues. Two main features likely contributed to the success of the method. First, the combinatorial library is robust; every possible combination of histidine and wild-type residue is sampled, thus providing an opportunity to co-select engineered variants that possess both high affinity binding and pH sensitivity. Second, the approach exploits the frequently observed plasticity of protein interfaces, a quality which is clearly apparent from the results, as approximately half the interface could tolerate histidine incorporation without loss of function.

A significant advantage of the combinatorial approach is that detailed structural knowledge of the antibody (or other protein of interest) is not required, only knowledge of the interface residues. For instance, the only structural information that was used in development of the anti-RNase A VHH histidine library was knowledge that CDR1 and CDR3 are involved in binding the RNase A target. Histidines were broadly sampled throughout CDR1 and CDR3, including both surface exposed and scaffolding residues. The approach can be easily modified to explore additional interface or scaffolding residues or leave specific residues unchanged. In fact, the method is completely scalable up to larger interfaces (e.g., conventional antibodies with interfaces possessing both heavy (VH) and light (VL) variable domains) where as many as 30-35 residues could be sampled by combining modern phage (Sidhu and Weiss, 2004) or mRNA (Lipovsek and Pluckthun 2004) display technologies with trinucleotide (trimer) phosphoramidite-based degenerate oligonucleotides (Fellouse et al. 2007).

Knowledge of the anti-RNase A VHH/RNase A complex structure allows a retrospective analysis into histidine "host" sites. Overall, an impressive amount of histidine incorporation was observed across the VHH interface; however, a distinct, centrally located group of 11 positions did not accommodate histidines, as seen in FIG. 4C. Nine of these residues (Y31, M34, G35, G99, G100, L103, T107, Y108, and G109) are predicted to be significantly buried in the absence of RNase A and contribute only 40 Å$^2$ of total surface area burial in the wild-type VHH/RNase A complex. The simplest explanation is that they cannot structurally tolerate a histidine substitution, due to their involvement in specific packing interactions which would be disrupted on histidine insertion. Similarly, the three glycine residues serve as "flexibility" points at the N- and C-terminal portions of the CDR3 loop, where insertion of a bulky histidine side chain would have detrimental effects on the conformation of the CDR3 loop for productive RNase A binding. Of the remaining two residues, D105 participates in an internal salt bridge with R45 that would be disrupted on histidine insertion, and T30 is likely located too far away from the RNase A interface (at least 8 Å).

In general, residues within the interface interior are poor histidine hosts, while the periphery residues appear well suited for histidine substitution. In particular, three histidine "hot-spots" (FIGS. 4C AND 4D) were identified by sequence analysis. VHH#10 possessed all three hot-spot histidines and displayed near wild-type affinity at pH 7.4 and an extremely sensitive pH binding profile (FIG. 5B). Such sequence analysis is particularly helpful in isolating pH sensitive clones. In general, histidine substitutions resulted in only minor structural changes in the VHH/RNase A complex as observed with the five histidine VHH#24/RNase A complex. The structure reveals that histidines serve as good "place keepers" for many types of residues, in particular tyrosine residues, which have comparable side chain size. This preference for tyrosine residues is significant for pH-dependent antibody engineering, as examinations of naturally derived antibodies reveal tyrosine residues play a prominent role in antibody binding sites by participating in approximately 25% of the antigen contacts. Consequently, tyrosine/histidine compatibility can easily be exploited for both screening- and nonscreening-based strategies to introduce new pH sensitivity.

Although a wild-type to histidine substitution inserts a protonation site, it is not necessarily sufficient to introduce pH dependence as the histidine must exhibit a $pK_a$ change on forming the protein-protein complex. There is no single structural "recipe" for such a change in proton affinity. A common finding is that the residue will experience a change in ΔASA between the bound and unbound states. In fact, the VHH interface sites that tolerate histidine substitutions are all located in regions where significant solvent surface area would be available in the unbound state. Many of these residues are predicted to experience significant change on binding RNase A, including surface area burial, loss of conformational freedom, as well as new electrostatic environments. The structure of the VHH#24/RNase A complex reveals that three of the five histidine residues Y29H, Y101H, and E102H are predicted to experience a change in environment based on surface burial; however, their specific contribution to pH sensitivity cannot be determined from structure alone. In addition, VHH#24's A28H/Y29H and Y101H/E102H paired interactions can also play a significant role, as histidine "pairs" are observed across many of the pH sensitive clones.

Through co-selection of both high-affinity antigen binding and binding sensitive protonation sites, this approach was extremely effective in generating a number of highly pH-dependent single chain VHH antibodies. Most importantly, these pH sensitive switches were made possible by the incorporation of many histidines with perturbed $pK_a$ values. First principles alone could not likely be used to identify several suitable histidines insertion sites. Therefore, the protein complexes described here will help serve as useful models to better understand the role of electrostatics in protein-protein recognition. This general approach performs well with other protein-affinity reagents. In fact, it is very likely that the number of histidine protonation sites can be further increased with larger interfaces, such as those found in conventional IgG, Fab, and scFv antibody fragments, which posses two variable domains (i.e., VH and VL). Because antibodies play a vital role in numerous applications, including diagnostics, therapeutics, and protein reagents, the ability to rapidly introduce pH-dependent control of binding holds exciting promise. Perhaps, even more interesting will be the potential of new applications where the binding of complex mixtures of antibodies, with differing pH profiles, can be controlled through slight modifications in pH.

Materials and Methods

Simulations: The pH dependence of the observed binding constant, $K_{obs}$, for a proton linked, protein-protein binding event was simulated using the following general relationship $$K_{obs} = K_{int}\frac{(1 + K_p^c[H])^n}{(1 + K_p^f[H])^n}$$

where $K_{int}$ is the protein-protein binding constant for the unprotonated species, $K_p^c$ and $K_p^f$ are the protonation binding constants (Kp=10 $pK_a$) for the ionizable group(s) in the complex and free states, respectively, and n is the number of ionizable histidine groups. Overall, this relationship assumes independent, noninteracting, protonation events. Simulated fits to the VHH#10 and VHH#24 include the following parameters. VHH#10 two histidine model:

$$pK_{a,1}^f = pK_{a,2}^f = 6.3, pK_{a,1}^c = pK_{a,2}^c = 2.0,$$

three histidine model:

$$pK_{a,1}^f = pK_{a,2}^f = pK_{a,3}^f = 6.3, pK_{a,1}^c = 5.5\ pK_{a,2}^c = 4.0, pK_{a,3}^c = 3.0,$$

VHH#24 two-histidine model:

$$pK_{a,1}^f = pK_{a,2}^f = 6.0, pK_{a,1}^c = pK_{a,2}^c = 2.0.$$

VHH#24 three histidine model:

$$pK_{a,1}^f = pK_{a,2}^f = pK_{a,3}^f = 6.0, pK_{a,1}^c = 5.5\ pK_{a,2}^c = 4.8, pK_{a,3}^c = 3.0,$$

Histidine Scanning Library Generation:

Starting with a phagemid vector containing the anti-RNase A VHH antibody fragment (cAb-RN05) upstream of the M13 gene MURT REFS 3,10, Kunkel mutagenesis MURT REFS 38 was used to create a binding incompetent VHH vector (phgmd-VHH-CDR13-stop) through the introduction of repeating stop codons throughout the CDR1 and CDR3 loops. Degenerate oligonucleotides (Sigma Genosys) were designed to encode both histidine and the original wild-type residue at each position within the CDR1 and CDR3 (CDR1: 5'-CGT CTG AGC TGC GCA GCA AGC SRTYATSMTYATMMTYATMWTYATMWKSRT TGG TTC CGT CAA GCA CCA GG-3' (SEQ ID NO: 1) and CDR3: 5'-CC TAC TAC TGC GCA GCA SRTSRTYATSAWCWTCRTSATCRTMMTYATSRTCAW TGG GGT CAA GGC ACC C-3' (SEQ ID NO: 2), where S=G/C, R=A/G, Y=C/T, K=G/T, M=A/C, W=A/T). For many residue positions, the degenerate codon library involved toggling a single pair of nucleotides, while some positions required varying more than one codon position to allow sampling of both wild-type and histidine side chains. Consequently, the corresponding residue position can sample nonwild-type or histidine side chains; however, their inclusion in the library will not affect selection. Kunkel mutagenesis (Kunkel et al. 1987) was used to generate the M13 phage library using the two histidine scanning oligonucleotides and single stranded deurycilated (dU-ssDNA) phgmd-VHH-CDR13-stop template using methods described previously. (Sidhu and Weiss, 2004). The histidine scanning library was verified through DNA sequencing.

Selection of pH Sensitive VHH Clones

Preparation of RNase A Target: RNase A (Sigma-Aldrich) was biotinylated using EZ-Link Sulfo-NHS-SS-Biotin (Pierce, Rockford). Briefly, RNase A (1 mg/mL) was dialyzed against 4 L of 50 mM phosphate buffer (pH 7.0). The Sulfo-NHS-SS-Biotin was dissolved in DMSO at a concentration of 1 mg/mL. The biotin solution and the RNase A solution were then mixed in a 1:9 ratio at room temperature for 45 minutes. After incubation, a ⅒ volume of 1M TRIS-HCl buffer (pH 8.0) was added to quench the reaction followed by overnight dialysis against 4 L PBS (pH 7.4). An aliquot was subjected to a pull-down test using magnetic streptavidin-coated beads (Promega, Madison Wis.). SDS-PAGE analysis was used to verify that RNase A was sufficiently biotinylated.

Phage Panning and Selection—The initial round of phage selection included incubation of the phage library ($10^{12}$ phage particles) with 2 µM biotinylated RNase A in TBS buffer (50 mM TRIS, 150 mM NaCl) pH 7.4. Phage that displayed binding competent VHH variants were then captured using magnetic streptavidin-coated beads (Promega, Madison Wis.) using a Kingfisher (Thermo Scientific) magnetic bead handler. Four wash steps were performed with TBS-Tween-20 buffer pH 7.4 to help eliminate non-specific interactions and weakly bound VHH variants. The phages bound to the beads are an example of a target binding population. pH sensitive VHH variants were selected by incubating the phage-bound beads in a low pH buffer (either pH 4.0 or 5.5). The eluted phage included the target-binding, pH sensitive VHH variants. This is an example of a modifiable target binding subpopulation. The eluted phage were amplified by first infecting a mid-log phase XL1-Blue (Stratagene) culture in 2×YT media (5 µg/mL tetracycline) for 20 minutes and then followed by inoculating a 30 mL overnight 2×YT culture (100 µg/mL Ampicilin, 5 µg/mL tetracycline, 0.2 mM IPTG, and $2.9 \times 10^{12}$ phage/ml M13K07 helper phage (New England Biolabs). The amplified, soluble phage were isolated by centrifugation (9,820×g; 10 minutes). The phage were then precipitated by diluting a 5× solution of 20% (w/v) PEG 8000, 2.5M NaCl. Precipitated phage particles were resuspended in TBS, pH 7.4 for the next round of selection. In effort to increase stringency for both high affinity pH 7.4 interactions and high pH sensitivity, over four rounds of selection, the concentration of the RNase A target decreased from 2 µM down to 20 nM, while the pH elution started at pH 4.0 and increased to pH 5.5 (50 mM Sodium Acetate/HCl, 150 mM NaCl). The progress of selection through each round (i.e. phage enrichment) was monitored through determination of phage titers.

ELISA Screening

Phage ELISA: Wells of a Maxisorp 96-well microtiter plate (Nunc) were coated with or without 2 µg/mL RNaseA in 50 mM PBS, 150 mM NaCl pH 7.4 and incubated overnight at 4° C. The plates were then blocked for one hour at room temperature with BSA (0.5%) in TBS. The plates were washed three times with TBST (TBS with 0.1% Tween-20), pH 7.4. Twenty-four clones were selected from phage screening and were diluted separately in either TBS, BSA (0.5%), Tween-20 (0.1%), pH 7.4 or TBS, BSA (0.5%), Tween20 (0.1%) pH 4.0. The phage were added to the washed plate and rotated at room temperature for thirty minutes. The plates were washed six times with TBST and two times with TBS followed by incubation with a 1:2500 dilution of HRP/Anti-M13 monoclonal antibody (GE Healthcare) for thirty minutes at room temperature with shaking. OPD substrate was added and the plate incubated for 30 minutes at room temperature in the dark. Reaction was quenched with 1M sulfuric acid. The optical absorbance was measured at 490 nm with a FLUOstar microplate reader (BMG Labtechnologies). Based in the initial ELISA data twelve clones were selected and sent out for sequencing.

Competitive Phage ELISA: Competitive phage ELISA's were performed as described by DeLano and Cunningham (DeLano and Cunningham 2004). Briefly, the concentration of phage needed to produce a 60% saturation signal was determined by running a phage ELISA of serially diluted phage stocks. This fixed amount of phage was then added to serially diluted RNase A and incubated for one hour at room temperature. The well contents of that plate were then transferred to a washed and blocked RNase A coated Maxisorp microtiter plate and incubated 15 minutes at room temperature. The plates were then treated as described above to determine the 490 nM absorbance. The IC50 values were then determined using Origin Labs using the following relationship:

$$f=(m3-m4)/((IC50/C)m2+1)+m4,$$

where f is the signal from bound phage, m2 is a slope constant, m3 is the maximal signal, m4 is the minimal signal, and C is the total competitor concentration.

To express the pH-sensitive VHH variants independently without the Gene-3 fusion, the VHH gene of interest was subcloned out of the phagemid vector and into a pET-21a expression plasmid (Novagen) using the primers (5'-GAGATATACATATGCATCATCATCATCATCATGAAAAC-CTGTACTTCCAGGG ATCCCAAGTACAACTGGTAG-3' (SEQ ID NO: 3)) and (5'-TAGACTCGAGGAATTCCTATT-AGCTGCTTACGGTTACTTGG-3' (SEQ ID NO: 4)), which introduce NdeI and EcoRI restriction sites along with an N-terminal hexa-His-TEV tag ("hexa-His" disclosed as SEQ ID NO: 5). Ligated clones were verified by DNA sequencing.

A 5-mL (LB/ampicillin) culture of E. coli BL21(DE3) containing pET-21a-HisTevVHH was grown overnight at 37° C. This culture was used to start a 50-mL subculture which, upon reaching mid-log phase, was used to inoculate a 1 L (LB/ampicillin) culture. VHH expression was induced with 1.0 mM isopropyl b-D-1-thiogalactopyranoside (IPTG) at optical density $(OD)_{600}$~0.5-0.8 and incubated at 20° C. overnight. The cells were isolated by centrifugation (17,700 g; 15 min) and subsequently frozen (−20° C.) overnight. The frozen pellet was then resuspended in 10 mM of TRIS pH 8.0 and sonicated (21 Watts) for three cycles of 2 min on/2 min off with a Model 60 Sonic Dismembrator (Fischer Scientific). As the VHH clones were expressed as insoluble inclusion bodies, the lysed cells were centrifuged (22,700 g; 20 min) to isolate the inclusion bodies/cell debris fraction. The pellet was washed with Tris-DE buffer [2% deoxycholic acid, 50 mM TRIS, 5 mM ethylenediaminetetraacetic acid (EDTA) pH 8.0], ddH2O and twice with 10 mM TRIS pH 8.0. The cells were centrifuged (22,700 g; 20 min) after each wash step and the resulting supernatant discarded. The final washed inclusion body pellet was resuspended in unfolding buffer (6M guanidine HCl, 50 mM NaPi/HCl, 300 Mm NaCl, 2.0-mM reduced glutathione (GSH), 0.2-mM oxidized glutathione (GSSG), pH 7.4) to solubilize the inclusion body and centrifuged (25,900 g; 20 min) to remove any insoluble material. Next, the unfolded VHH was refolded by dropwise addition to refolding buffer (20 mM TRIS-HCl, 2.0 mM GSH, 0.2 mM GSSG, pH 7.4) at 4° C. with moderate stirring. The final refolded solution corresponded to a 10 dilution of the unfolded protein. Refolded protein was centrifuged (25,900 g; 15 min) to remove insoluble precipitate. The refolded VHH protein was subsequently purified as described previously (Sonneson and Horn 2009).

Isothermal Titration Calorimetry

All experiments were run with a VP-ITC titration calorimeter (MicroCal). Buffer matching was ensured by dialyzing the VHH variant and bovine RNase A (Sigma-Aldrich) overnight in 4 L of buffer at 4° C. Buffer conditions depended on the pH of the experimental run. All buffers contained 150 mM NaCl and 20 mM buffer. Buffers and their pH ranges included: phosphate (pH 6.0-7.4), TRIS (pH 8.0-9.0), acetate (pH 3.0-5.5), and piperazine (pH 4.3-6.3). Protein concentrations were determined by UV absorbance using a UV-visible spectrometer (Hewlett Packard). Extinction coefficients (280 nm) were 9,440 M-1 cm$^{-1}$ (RNase A), 22,091 M-1 cm-1 (VHH#24), and 21,555 M-1 cm-1 (VHH#10). Extinction coefficient values were determined using methods described by Pace et al. (1995). For high-pH/highaffinity experiments, titrations were performed with VHH as the titrant at concentrations over a range of 40-200 µM. RNase A concentrations were typically one-tenth the respective concentration of VHH. For low-pH/low-affinity experiments, the methods of Turnbull and Daranas (2003) were followed. Generally, RNase A was used as the titrant at a concentration of 1 mM, and VHH concentration was 100-fold lower. To find conditions that gave sufficient heats of binding, a range of temperatures and buffers was used. Experiments were run at 25° C. from Ph 6 to 8 and 10° C. from pH 5.5 to 4.5 with VHH as the titrant. With RNase A as the titrant experiments were run at 25° C. from pH 4.7 to 4.5. Dilution experiments (titrant into buffer) were performed to account for heats of dilution. Data were analyzed using Origin with the Microcal ITC add-on available from the manufacturer.

Circular Dichroism

All experiments were run with an Aviv Instruments circular dichroism spectrometer model 215. Wavelength scans were carried out at 25° C. from 240 to 200 nm in phosphate buffer saline (PBS) (10 mM sodium phosphate, 150 mM sodium chloride, pH 7.4, pH 3.0, or pH 2.0) and acetate (10 mM sodium acetate, 150 mM sodium chloride pH 4.0 or pH 5.5). A quartz cuvette was used with a 1-mm path length. Temperature denaturation experiments were carried out at 207 nm from 25 to 85° C. at 1° increments. The Tm values were then determined with Origin Labs.

Structure Determination of the Anti-RNase A VHH#24/RNase A Complex

About 20 mg mL-1 of anti-RNase A VHH#24 TBS (10 mM Tris, 300 mM NaCl, pH 8.0) was mixed equally with 25 mg mL$^{-1}$ bovine RNase A (Sigma-Aldrich). The complex was run through a 10/30GL Superdex-75 size exclusion column (GE Healthcare), and the peak corresponding to the VHH/RNase A complex was collected. Crystallization was performed by the hanging drop method by mixing 2 L of the 20 mg mL$^{-1}$ VHH-RNase A solution with 2 µL of 0.2M lithium sulfate monohydrate, 0.1M bis-tris pH 5.5, 25% w/v polyethylene glycol 3,350 (Hampton Research, Aliso Viejo, Calif.). X-Ray data were collected at Southeast Regional Collaborative Access Team (SER-CAT), 22-BM beamline at the Advanced Photon Source, Argonne National Laboratories. Glycerol (20%) was used as a cryoprotectant. Data were indexed, merged, and scaled using HKL-2000 (Otwinowski and Minor 1997). The CCP4 suite was used to generate the initial electron density, as well as perform molecular replacement (phaser) (Collaborative Computational Project 1994). The initial search model for molecular replacement was the anti-RNase A VHH/RNase A complex, PDB ID: 2P49. A single VHH#24/RNase A complex was found within the asymmetric unit. Data were refined using CCP4's Refmac. Model building was performed using the program Coot (Emsley and Cowtan 2004). The three complementary determining regions were initially removed from the structure and subsequently rebuild. Residues 16-22 of RNase A are not included in the model due to lack of electron density. These residues are also missing in other anti-RNase A VHH/RNase A crystal structures (Decanniere et al. 1999, Koide et al. 2007). Crystallographic statistics are presented in Table 2. The structure is assigned PDB ID code 3QSK. Structure models were generated with Pymol.45.

EXAMPLE 2

Design and Engineering of Metal Dependent Molecular Switch Functionality into an Antibody Biology employs a number of strategies to regulate protein binding events, but the underlying principle behind most regulation is simply coupled equilibria. A minimalist example of such linked equilibria-based regulation involves a single (common) protein interface that is capable of recognizing more than one target. Such promiscuous protein binding can serve to enhance or preclude secondary binding events and frequently plays a role in regulating signaling pathways. In general, the underlying structural properties of such dual-specific protein interfaces are not well understood as the types of interactions that are necessary for each binding event may be significantly different.

Metal binding proteins are among the most commonly observed dualspecific proteins. Traditional efforts to design novel metal binding sites rely heavily on knowledge of the protein's three-dimensional structure. Furthermore, most design efforts introduce metal binding sites within rigid protein scaffolding, such as helices or at the interface of oligomeric states of helical bundle proteins and not typically within loop regions.

FIG. 9 depicts the underlying linked equilibria model, where $K_{int}$ and Kmetal are the antigen and metal binding equilibrium constants, respectively. Antibody recognition of the two targets, antigen and metal, is mutually exclusive, which results in an overall observed antigen binding constant, $K_{obs}$, that is dependent on metal concentration. The histidine-scanning anti-RNAse A VHH library, discussed in Example 1, introduces metal sensitive molecular switch functionality into the VHH-RNAse interface. Phage display selection was performed as in Example 1; however, instead of low pH, elution buffer contained a 10 mM mix of $Zn^{2+}$, $Co^{2+}$, and $Ni^{2+}$. To maintain the anti-RNase A VHH's high affinity ($K_d$~20 nM), the first round of phage panning selected variants that solely recognized RNase A. Over the next three rounds of selection, VHH presenting phage were initially selected for RNase A binding, followed by competitive selection of metal sensitive VHH clones using the metal ion mixture. To increase the stringency of selection of binding both RNase A and metal, the concentrations of VHH and metal were decreased each round. After four total rounds of selection, immunoassay screening allowed identification of a metal sensitive anti-RNase A VHH clone, termed "VHH-metal".

In competitive ELISA, performed as in Example 1, VHH-metal displayed a 1000-fold change in IC(50) values as compared to wild-type VHH with and without 1 mM metals (FIG. 10A). DNA sequencing revealed that the feature which distinguished the target-binding interface of VHH-metal from the wild type VHH interface was three histidine substitutions, Y29H, Y33H, and Q110H (FIGS. 10B and 10C). These substitutions therefore constituted the molecular switch motif for the metal sensitive VHH.

To examine VHH-metal's specificity, circular dichroism (CD) was used to monitor thermal stability in the absence or presence of each metal (1 mM) used during screening (i.e., cobalt, nickel, and zinc). An increase in the melting temperature, $T_m$, of approximately 7° C. was observed in the presence of 1 mM nickel (FIG. 11A), whereas smaller shifts in $T_m$ were observed in the presence of either zinc or cobalt (not shown). Consequently, nickel was used for all subsequent experiments. Control experiments revealed the thermal stability of the wild-type anti-RNase A VHH was unchanged in the presence and absence of 1 mM nickel (FIG. 11B), indicating the nickel binding was due to the remodeled interface. Similarly, control experiments with the antigen, RNase A, with and without metal, displayed no change in $T_m$ (data not shown). Comparison of the thermal unfolding of VHH-metal to the original anti-RNase VHH, in the absence of metal, revealed that the remodeled metal interface resulted in a decrease in $T_m$ by ~4° C. (FIGS. 11A AND 11B).

Isothermal titration calorimetry (ITC) was used to evaluate the thermodynamic basis for VHH-metal's dual function. FIG. 12A displays titrations of nickel into VHH-metal, which revealed a metal binding dissociation constant, $K_d$, of 30±10 µM. This value is comparable to affinities reported for other nickel binding proteins. As expected, titrations of nickel into wild-type anti-RNase A VHH produced no measurable binding. In the absence of metal, VHH-metal possessed a slightly decreased binding affinity for RNase A ($K^d$=155±5 nM) compared to that of wild type anti-RNaseA VHH (Kd=19±1 nM), which corresponds to an ~8-fold decrease in binding affinity ($\Delta\Delta G°$=1.2 kcal/mol). Overall, the thermodynamic basis for binding to RNase A did not dramatically change versus the wild-type anti-RNase A VHH, where recognition of RNase A is primarily based on a favorable enthalpic contribution overcoming an unfavorable entropic penalty (Tables 3 and 4).

To determine whether metal binding could compete with RNase A binding, VHH-RNase A binding was examined over a range of nickel ion concentrations (10 µM to 10 mM). As displayed in FIG. 12B, the observed binding constant, $K^{obs}$, is clearly influenced by the presence of increasing concentrations of nickel. Fitting the model (FIG. 9) to the data revealed a metal binding constant, $K^{metal}$, of (4.3±0.8)× 104 ($K^d$=23±5 µM), which is within error of the metal binding constant measured independently. Overall, this suggests that formation of the metal binding site must significantly perturb and/or block the RNase A binding site.

Existing knowledge of the wild-type anti-RNase A-VHH-RNase A complex structure provides insight into how the VHH interface may accommodate a metal binding site yet retain the ability to bind RNase A. Overall, the distances between the Cα atoms for the three inserted histidines, H29, H33, and H110, all fall between 11 and 14 Å. These distances are within commonly expected ranges for metal binding sites. In addition, it is possible that residue(s) preexisting in the interface may contribute as metal ligands, e.g., Q1, D52, D73, E102, and D105 (see FIG. 10B). Consequently, the engineered metal binding site is likely to use at least two histidines and may include preexisting residues. Of the three histidine substitutions, Y29H and Q110H are located in solvent accessible positions, while Y33H would be predicted to participate in significant intramolecular contacts at the C-terminal end of CDR1 (FIG. 10B). Consequently, it is predicted that the Y33H substitution would be conformationally restricted in its ability to form a metal binding site, while Y29H and 110H substitutions would be better posed to form a metal site. Finally, note that the metal site is specific for nickel, as titrations performed in the presence of calcium ions did not show any appreciable change in the observed binding constant.

Perhaps the most interesting feature of the engineered metal binding complex is that it must induce significant structural change and/or steric restriction that is capable of prohibiting RNase A binding, while not adversely affecting RNase A binding in the absence of metal. Clearly, conformational flexibility of the CDRs appears to be advantageous for the acquired dual specificity. Furthermore, of the three substitution sites (Y29H, Q110H, and Y33H), two of the substituted residues are tyrosines. Such isosteric substitution may be common when acquiring dual-specific binding properties, as long as the replacement residues serve as useful "filler" residues. Also, all substituted H is residues are located in peripheral positions. For instance, upon formation of the wild-type complex, only Y33 buries significant surface area (through van der Waals contacts). Future structural and biophysical studies will be necessary to investigate the role that specific residues and loop conformation play in metal binding affinity and specificity.

It is perhaps somewhat surprising that only a single metal binding VHH clone was identified. This may due to excessively stringent selection. Alternatively, it is likely that the introduction of additional interface metal ligands (e.g., Glu, Asp, etc.) may ultimately be necessary to develop higher-affinity metal binding sites. Such metal binding sites will provide new routes in which to modulate protein binding.

Protein interactions can be controlled through simple ligand binding, such as the binding of metal ions. Two general examples of ligand coupled binding are presented in FIG. 13, where ligand binding results in stabilization of either a binding incompetent or a binding competent state. In order to create protein affinity reagents whose affinity for target decreases in the presence of ligand, variants are selected for the stabilization of a binding incompetent state by the ligand. To create protein affinity reagents whose affinity for target is enhanced by increased ligand, variants are selected for the stabilization of a binding competent state by the presence of ligand.

For example, to select phage displaying the VHH metal binding library, the library can be panned using two methods. To select variants whose affinity for target is decreased by metal (FIG. 13, at "A"), a His/Asp/Glu/Wt library is exposed to 20 nM RNase A (biotinylated) under physiological buffer conditions (pH 7.4). VHH phage which bind to biotinylated RNase A are pulled down using streptavidin coated magnetic beads. After performing several wash steps to remove non-binding phage, metal binding VHH phage are eluted though incubation of the streptavidin captured phage with a 10 mM metal mix (Ni2+, Co2+, Zn2+). Eluted phage are amplified and subjected to two to four additional rounds of selection. To select variants whose target affinity is enhanced in the presence of ligand, (FIG. 13 at "B"), phage screening follows a more traditional approach, where the target (RNase A) concentration is decreased in a step-wise fashion with each round, to increase the stringency of the screen, thereby capturing the highest affinity binders. In this method, the metal mix remains in all solutions (i.e., binding and wash buffers). High affinity clones are eluted with EDTA or DTT (to disrupt the biotin dithiol linkage).

Materials and Methods

VHH Library Generation

To introduce a metal binding site within the anti-RNase A VHH interface, a library was generated that introduces histidine residues throughout the binding interface similar to a method used to introduce pH dependence into a metal binding interface. Starting with a phagemid vector containing an anti-RNase A VHH gene upstream of M13 Gene 3, Kunkel mutagenesis was used to introduce stop codons within the two binding interface loops, CDR1 (Kabat Residues #26-35) and CDR3 (Residues #99-100J). Next, degenerate primers were designed such that 22 interface residues within CDR1 and CDR3 would be either the wild-type residue or a histidine using the following oligonucleotides. CDR1: CGTCTGAGCTGCGCAGCAAGC SRTYATSMTYATMMTYATMWTYATMWKSRT TGGT-TCCGTCAAGCACCAGG (SEQ ID NO: 1). CDR3: CC TAC TAC TGC GCA GCA SRT SRTYATSAWCWTCRTSATCRTMMTYATSRTCAW TGG GGT CAA GGC ACC C (SEQ ID NO: 2), where S=C/G, R=A/G, Y=C/T, M=A/C, W=A/T, K=G/T. Underlined sequences represent interface positions that sample histidine/wild-type. While some positions allowed simple binary diversity, consisting only of histidine and wild-type, there were several positions that required the introduction of degeneracy in more than one codon position to allow sampling of wild-type and histidine residues. While this significantly increased the theoretical diversity of the library ($10^{10}$ unique members as compared to $10^6$ for a simple binary library), the theoretical diversity is within the range that can fully be sampled using phage display. Ultimately, the inclusion of these non-wild-type/non-histidine residues do not affect the ability to sample metal sites across the interface. The phage particles were produced as described by Sonneson.

Selection of Metal Dependent VHH Clones

Preparation of Biotinylated RNase A Target—Bovine pancreatic RNase A was biotinylated using EZ-Link Sulfo-NHS-SS-Biotin (Pierce, Rockford, Ill.) according to the manufacturer's instructions. Biotinylation was verified using a pull-down test with streptavidin-coated paramagnetic beads (Promega, Madison, Wis.).

Dual Function Phage Selection—The first round of selection aimed to select VHH variants which recognized RNase A. 1 mL of the his-scan library ($1 \times 10^{12}$ phage/mL titer) was incubated for 10 minutes with shaking at room temperature with 10 µM biotinylated RNase A and EDTA in TBS (20 mM Tris, 150 mM NaCl pH 7.4). Then, 50 µL of washed streptavidin-coated paramagnetic beads were added to the reaction. After rotating for 10 minutes at room temperature, the beads were harvested by centrifugation at 13.1 k×g for 2 minutes. The tube was placed in a magnetic rack and the supernatant was discarded. The beads were washed three times in TBS and brought up to a final volume of 100 µL in TBS-D (20 mM Tris-HCl, 150 mM NaCl, 100 mM DTT, pH 7.4) and mixed for 15 minutes at room temperature to elute the bound phage particles. Output phage particles were used to infect mid-log phase XL-1 blue *E. coli.* and amplified following previously published protocols (Sidhu and Weiss, 2004).

The next three rounds of phage display were performed utilizing a King Fisher magnetic particle processor (Thermo Scientific). Phage particles were incubated with biotinylated RNase A in TBS then captured with 50 µL, streptavidin-coated magnetic beads, which were washed three times in TBS-T (20 mM Tris, 150 mM NaCl, 0.1% w/v Tween-20, pH 7.4), and eluted with metal mixture containing cobalt, nickel, and zinc. Three rounds were performed with the concentration of biotinylated RNase A decreasing from 1 µM to 10 nM and a mixture of cobalt, nickel and zinc, decreasing in concentration from 100 µM to 10 µM. Phage were amplified after each round of selection as described previously (4). After the 4$^{th}$ round of selection, infected XL-1 blue cells were plated and individual clones were harvested as described. The DNA of 18 clones was sent for sequencing, which revealed only a single metal binding clone was present. (FIG. 8).

VHH Expression and Purification

The single, metal-sensitive, anti-RNase A VHH clone was moved into a pET-21a(+) expression plasmid vector (Novagen) using subcloning. Primers for EcoRI reverse (5-TAGACTCGAGGAATTCCTATTAGCTGCTTACGGT-TACTTGG-3'(SEQ ID NO: 4)) and NdeI forward, containing an insert corresponding to a Hexahis-Tev N-terminal tag ("Hexahis" disclosed as SEQ ID NO: 5), (5'-GAGATATA-CATATGCATCATCATCATCATCATGAAAACCTG-TACTTCCAGGG ATCCCAAGTACAACTGGTAG-3' (SEQ ID NO: 3)) were used to introduce restriction sites. DNA sequencing was used to verify the correct ligation of the metal-sensitive anti-RNase A VHH in pET21a(+).

The metal-binding VHH clone was expressed in BL21 (DE3) *E. coli.* Briefly, a 5 mL starter culture of LB/amp was innoculated and allowed to grow overnight at 37° C. The next morning, 1 mL from the overnight culture was used to inoculate a 50 mL subculture of LB/amp. Upon reaching mid-log phase growth ($OD_{600}$ 0.5-0.8) the culture was used to inoculate 1 L of LB/amp. Once the cells reached mid-log phase they were induced with 1 mM IPTG and allowed to express overnight at 20° C. Cells were harvested by centrifugation (7,500×g for 15 minutes at 4° C.) and frozen. The cell pellet was thawed and resuspended in 20 mM TRIS, pH 8.0 and sonicated (21 Watts) for three 2 minute on/off cycles with a Model 60 Sonic Dismembranator (Fischer Scientific). The mixture was centrifuged (8,500×g for 20 minutes at 4° C.) and the supernatant was discarded to isolate the insoluble fraction containing VHH. The inclusion body pellet was washed with 50 mL 2% deoxycholic acid, 50 mM Tris, 5 mM EDTA pH 8.0, then with deionized water, and a final time with 10 mM Tris pH 8.0. The resulting washed inclusion body pellet was then solubilized with 50 mL unfolding buffer (6 M Guanidine HCl, 50 mM Sodium Phosphate, 300 mM NaCl, 2 mM reduced glutathione, and 0.2 mM oxidized glutathione at pH 7.4). The solution was clarified through centrifugation and then added drop-wise to 500 mL of refolding buffer (20 mM TRIS, 2 mM reduced glutathione, 0.2 mM oxidized glutathione at pH 7.4) overnight with mixing at 5° C. Purification of the metal clone VHH and removal of the His-TEV tag was performed as previously described by Sonneson and Horn, 2009.

Circular Dichroism

All CD experiments were performed on an Aviv Instruments circular dichroism spectrometer model 214. Proteins were dialyzed overnight in 10 mM sodium phosphate and 150 mM NaCl pH 7.4 at 5'C. The VHH was at a concentration between 29 µM and 33 µM for each CD experiment. A stock solution of the given metal made at 10 mM concentration in the same dialysis buffer was added to the cuvette for a final concentration between 0.1 mM and 1 mM. A 1 mm path length quartz cuvette was used for all data collection. Thermal melts were performed by increasing the temperature from 25° C. to 85° C. with 1 minute equilibrations at each degree (ramp rate 1° C./min). Protein unfolding was monitored by observing the change in signal at 217 nm, using a 1 nM bandwidth and a 1 mm slit. All data were fit using a two-state unfolding model in Origin Labs.

Isothermal Titration Calorimetry

ITC experiments were performed using a MicroCal VP-ITC (MicroCal, LLC, Northampton, Mass.). All experiments were performed at 25° C. Proteins were dialyzed against the desired experimental buffer, which included PBS (20 mM NaPhosphate, 150 mM NaCl pH 7.4), TBS (20 mM Tris-HCl, 150 mM NaCl pH 7.4) and TBS-E (20 mM Tris, 150 mM NaCl, 1 mM EDTA, pH 7.4). For direct titration of $NiCl_2$ into the VHH-metal variant, concentrations were 2 mM and 200 µM for NiCl2 and VHH, respectively. Based on the observed binding constant, this corresponds to a "c-value" of 6.7, which is within the commonly acceptable range for the accurate determination of binding thermodynamics. For competitive titrations, nickel was included in TBS without EDTA at concentrations ranging from 0-10 mM. Competitive VHH/RNase A titration experiments with a "c" value greater than 10 included protein concentrations ranging from 30 µM to 205 µM. Conditions included a 10-fold higher concentration of titrant (VHH). Experiments possessing a "c" value less than 10 were performed following methods described previously. These experiments included using a 100-fold higher concentration of titrant (RNase A) relative to VHH. RNase A concentrations were between 150 µM and 800 µM. Extinction coefficients were determined using values determined by the methods described by Pace, et. al. The extinction coefficient of RNase A was 9,440 $M^{-1}$ $cm^{-1}$, 23,045 $M^{-1}$ $cm^{-1}$ for the metal sensitive anti-RNase A VHH, and 24,595 $M^{-1}$ $cm^{-1}$ for the wild-type anti-RNase A VHH. For nickel/VHH titrations, the titrant nickel was dissolved in the appropriate dialysis buffer at a 10× concentration of the VHH. Experiments typically included 27, 10 µL injections with a 240 second delay between each injection. Dilution titrations indicated the absence of significant heats of dilution, consequently, no background dilution heat subtractions were necessary. The binding parameters (K, $\Delta H°$, $\Delta S°$, and n) were determined using the single site binding model using the ITC add-in in Origin version 7 (MicroCal LLC). All titrations indicated a 1:1 interaction with observed stoichiometries equal to 1.0 (within 5%).

Materials and Methods

Output VHH Analysis and Interpretation of Results

Phage displaying metal sensitive VHH binding are initially screened through traditional and competitive ELISA assays and DNA sequencing. Based on these assays, select clones are small-scale expressed and purified, as described above, to allow determination of quantitative binding information using surface plasmon resonance (SPR). Additionally, as the phage screening approach uses a metal ion mixture, specific preferences for certain metal ions are determined at this phase.

The structure and behavior of variant clones with molecular switch functionality can then be explored to aid the rational design of molecular switch motifs. Clones which display strong metal binding dependence can be further analyzed using isothermal titration calorimetry (ITC) to obtain and dissect the thermodynamic parameters of each contributing equilibrium. Variants that display strong metal dependence can also be subjected to crystal structure analysis, whether of the free VHH species or the VHH/RNase A complex.

Selection of Metal Dependent VHH Clones

Preparation of a histidine-scanning VHH library, and of biotinylated RNase A target: beads were performed as described in Example 1.

Dual Function Phage Selection: The first round of selection was aimed to select VHH variants which recognized RNase A. 1 mL of the his-scan library (1×1012 phage/mL titer) was incubated for 10 minutes with shaking at room temperature with 10 µM biotinylated RNase A and EDTA in TBS (20 mM Tris, 150 mM NaCl pH 7.4). Then, 50 µL of washed streptavidin-coated paramagnetic beads were added to the reaction. After rotating for 10 minutes at room temperature, the beads were harvested by centrifugation at 13.1 k×g for 2 minutes. The tube was placed in a magnetic rack and the supernatant was discarded. The beads were washed three times in TBS and brought up to a final volume of 100 µL in TBS-D (20 mM Tris-HCl, 150 mM NaCl, 100 mM DTT, pH 7.4) and mixed for 15 minutes at room temperature to elute the bound phage particles. Output phage particles were used to infect mid-log phase XL-1 blue E. coli. and amplified following previously published protocols (Sidhu and Weiss, 2004).

The next three rounds of phage display were performed utilizing a King Fisher magnetic particle processor (Thermo Scientific). Phage particles were incubated with biotinylated RNase A in TBS then captured with 50 µL, streptavidin-coated magnetic beads, which were washed three times in TBS-T (20 mM Tris, 150 mM NaCl, 0.1% w/v Tween-20, pH 7.4), and eluted with metal mixture containing cobalt, nickel, and zinc. Three rounds were performed with the concentration of biotinylated RNase A decreasing from 1 µM to 10 nM and a mixture of cobalt, nickel and zinc, decreasing in concentration from 100 µM to 10 µM. Phage were amplified after each round of selection as described previously (Sidhu and Weiss, 2004). After the 4th round of selection, infected XL-1 blue cells were plated and individual clones were harvested as described. The DNA of 18 clones was sent for sequencing, which revealed only a single metal binding clone was present (FIG. 10C).

VHH Expression and Purification: The single, metal-sensitive, anti-RNase A VHH clone was moved into a pET-21a(+), expressed BL21 (DE3) E. coli, and the metal clone VHH was purified, according to the methods described in Example 1, including the same sets of PCR primers.

Circular Dichroism: All CD experiments were performed on an Aviv Instruments circular dichroism spectrometer model 214. Proteins were dialyzed overnight in 10 mM sodium phosphate and 150 mM NaCl pH 7.4 at 5° C. The VHH was at a concentration between 29 µM and 33 µM for each CD experiment. A stock solution of the given metal made at 10 mM concentration in the same dialysis buffer was added to the cuvette for a final concentration between 0.1 mM and 1 mM. A 1 mm path length quartz cuvette was used for all data collection. Thermal melts were performed by increasing the temperature from 25° C. to 85° C. with 1 minute equilibrations at each degree (ramp rate 1° C./min). Protein unfolding was monitored by observing the change in signal at 217 nm, using a 1 nM bandwidth and a 1 mm slit. All data were fit using a two-state unfolding model in Origin Labs.

Isothermal Titration Calorimetry: ITC experiments were performed using a MicroCal VP-ITC (MicroCal, LLC, Northampton, Mass.). All experiments were performed at 25° C. Proteins were dialyzed against the desired experimental buffer, which included PBS (20 mM NaPhosphate, 150 mM NaCl pH 7.4), TBS (20 mM Tris-HCl, 150 mM NaCl pH 7.4) and TBS-E (20 mM Tris, 150 mM NaCl, 1 mM EDTA, pH 7.4). For direct titration of $NiCl_2$ into the VHHmetal variant, concentrations were 2 mM and 200 µM for NiCl$_2$ and VHH, respectively. Based on the observed binding constant, this corresponds to a "cvalue" of 6.7, which is within the commonly acceptable range for the accurate determination of binding thermodynamics (Tellinghuisen, 2008; Wiseman et al. 1989). For competitive titrations, nickel was included in TBS without EDTA at concentrations ranging from 0-10 mM. Competitive VHH/RNase A titration experiments with a "c" value greater than 10 included protein concentrations ranging from 30 µM to 205 µM. Conditions included a 10-fold higher concentration of titrant (VHH). Experiments possessing a "c" value less than 10 were performed following methods described previously (Turnbull and Daranas 2003). These experiments included using a 100-fold higher concentration of titrant (RNase A) relative to VHH. RNase A concentrations were between 150 µM and 800 µM. Extinction coefficients were determined using values determined by the methods described by Pace, et. al. (1995). The extinction coefficient of RNase A was 9,440 M$^{-1}$ cm$^{-1}$, 23,045 M$^{-1}$ cm$^{-1}$ for the metal sensitive anti-RNase A VHH, and 24,595 M$^{-1}$ cm$^{-1}$ for the wild-type anti-RNase A VHH. For nickel/VHH titrations, the titrant nickel was dissolved in the appropriate dialysis buffer at a 10× concentration of the VHH. Experiments typically included 27, 10 µL injections with a 240 second delay between each injection. Dilution titrations indicated the absence of significant heats of dilution, consequently, no background dilution heat subtractions were necessary. The binding parameters (K, ΔH°, ΔS°, and n) were determined using the single site binding model using the ITC add-in in Origin version 7 (MicroCal LLC). All titrations indicated a 1:1 interaction with observed stoichiometries equal to 1.0 (within 5%).

EXAMPLE 3

Generation of an Anti-Hapten VHH Antibody and Characterization of its Binding Thermodynamics Traditionally, anti-hapten antibodies are generated by injecting the small molecule of interest coupled to a larger protein, a carrier, to elicit an immune response against the injected species. Such antibodies often display low affinity and specificity for the hapten, at least partly because the covalent tethering of the large carrier sterically prevents full antibody recognition of the small hapten.

While VHH domains have rivaled conventional antibodies in terms of their affinity for protein antigens, much less is known regarding their ability to bind small haptens. To address this gap, the three CDRs of a recently generated anti-caffeine VHH antibody were grafted onto the anti-RNase A VHH domain, discussed in Examples 1 and 2. The resulting anti-caffeine VHH was optimized for recombinant E. coli expression and purification, which produced high VHH yields (~60 mg/L of culture).

Biophysical properties of caffeine/anti-caffeine VHH binding, Isothermal titration calorimetry (ITC) was performed to provide a full thermodynamic profile of binding (Kb, ΔG°, ΔH°, and ΔS°) (FIG. 15A). Binding is enthalpically-driven (ΔH°=−14 kcal/mol) and overcomes a small entopic penalty (−TΔS°=3.9 kcal/mol), leading to an overall ΔG° of −10 kcal/mol (Kb,obs=7.1×10$^7$). The observed Kb is quite large (favorable), corresponding to a Kd value of 20 nM. However, the most striking feature was the observed 2:1 binding stoichiometry. A large ΔCp of binding and size exclusion chromatography profile further support this unconventional 2:1 binding stoichiometry between the anti-caffeine VHH and caffeine, respectively (FIGS. 14 and 15B). The binding of three caffeine metabolites (theophylline, paraxanthine, and theobromine) displayed a ~50-fold range in binding, yet maintained the 2:1 stoichiometry. (Franco et al. 2010)

All experiments were run with a VP-ITC titration calorimeter (MicroCal). Buffer matching was ensured by dialyzing the VHH variant and bovine RNase A (Sigma-Aldrich) overnight in 4 L of buffer at 4° C. Buffer conditions depended on the pH of the experimental run. All buffers contained 150 mM NaCl and 20 mM buffer. Buffers and their pH ranges included: phosphate (pH 6.0-7.4), TRIS (pH 8.0-9.0), and acetate (pH 3.0-5.5). Protein concentrations were determined by UV absorbance using a UV-visible spectrometer (Hewlett Packard). Extinction coefficients (280 nm) were 9440 M$^{-1}$ cm$^{-1}$ (RNase A) and 21615 M$^{-1}$ cm$^{-1}$ (VHH 5-His ("5-His" disclosed as SEQ ID NO: 6)). Coefficient values were determined by methods described by Pace, et. al. (Pace, Vajdos et al. 1995). Titrations were performed with VHH as the titrant at concentrations over a range of 40 uM to 100 uM. RNase A concentrations were one-tenth the respective concentration of VHH. All experiments were run at 25° C. Data were analyzed using Origin with the Microcal ITC add-on available from the manufacturer.

Structure Determination of the Anti-caffeine VHH/Caffeine 2:1 Complex

High resolution (to 1.1 Å resolution) x-ray data of the VHH/caffeine complex resolved several features of the interaction. First, the crystal structure agrees with the 2:1 VHH/caffeine stoichiometry, as two VHH molecules come together to sandwich the caffeine ligand (FIGS. 16A and 16B). The two VHH domains are oriented by a 2-fold symmetry rotation, reminiscent of a conventional VH/VL interaction. Interestingly, in the process of forming the caffeine complex, the CDR3 loops of both VHH molecules are displaced from their canonical VHH positioning (FIG. 16C). This movement appears to allow the exposure of new surface area for recognition of caffeine, which also correlates with a lower than expected observed thermostability profile (data not shown).

These findings have been extended to the generation of antimethotrexate VHH which bind the drug methotrexate at three different sites.

In Vitro Selection Methods to Generate Anti-hapten Antibodies (FIG. 14).

The findings discussed above lead to a method for generating antihapten affinity reagents with dramatically greater affinity than either VHH domain alone, or than a conventional antibody containing two identical variable domains. Briefly, a protein library of VHH domains is created by techniques well known in the art, for example those disclosed in Examples 1 and 2. The VHH domains are preferably soluble and biotinylated. The VHH are incubated with the haptens, preferably in solution. VHH domains that bind recognition sites on the hapten form VHH-hapten complexes. These are termed first VHH-hapten 1 complexes, wherein a first VHH binds a first recognition site on the hapten. At least one first VHH-hapten complex is captured, preferably by streptavidin coated beads or substrate. As an alternative to capturing and identifying the first VHH-hapten 1 complex using a library, it is possible to start with an existing VHH-hapten 1:1 complex (or any small molecule-protein interaction). This "complex" then becomes the "target" of screening a library of VHH variants that will be used to find the subset of the library that will form the 2:1 complex. Next, a second VHH domain which specifically binds the first VHH-hapten complex is selected from the same expression library, or alternatively from a different library tailored to target likely second recognition sites on the hapten. The second VHH is selected on the basis of its ability to bind the first VHH-hapten complex. The combination of the second VHH and the first VHH-hapten complex is termed the second VHH-hapten complex. The second VHH-hapten complex is purified, the first and second VHH domains are characterized, and the combination of first and second VHH domains is identified as a protein affinity reagent against the hapten. Preferably, the first and second VHH domains are cloned into expression vectors for the production and purification of the first and second VHH domains. The first and second VHH domains could then be covalently coupled, similar to scFv antibody fragments, or potentially crosslinked, such as engineered disulfides. Simply having the second VHH which recognized the VHH-hapten complex provides a method to modulate/regulate (enhancing) hapten recognition.

This method of generating high affinity anti hapten antibodies is readily adapted for use with any hapten or protein affinity reagent. Libraries of camelid VHH domains are preferred, but any libraries of any single chain antibody can be used as the basis for generation of variants for selection. Of course, once a high affinity antibody is created for a given hapten, it can be further enhanced by the introduction of molecular switch functionality, using the methods and compositions described in detail in Examples 1 and 2.

Reduced codon libraries (or even natural libraries from an animal host) are used, not "ionizable residue" libraries. The overlap/similarity with the pH and metal examples herein is that in vitro selection allows targeting a non-covalent protein-hapten complex. This is novel and is ultimately guided by the coupled equilibria (similar to pH and metal dependence examples). Generating an antibody which recognizes an antibody/hapten complex dramatically enhances the observed binding affinity by many orders of magnitude.

EXAMPLE 4

Design and Engineering of an "Inverse" pH Dependent Molecular Switch Functionality into an Antibody Example 1 presented the generation of a protein affinity reagent that possessed a binding affinity for its target molecule that decreased as the pH was decreased from 7 to 4. An alternate pH-dependent binding profile is possible, referred here as an "inverse" pH sensitive switch. In this scenario, the binding constant decreases, not by decreasing the pH, but by increasing the pH (FIG. 18). To generate the inverse pH switch, a synthetic, combinatorial library was constructed using oligonucleotide-directed mutagenesis in a manner similar to that described in Example 1. However, this library sampled acid residues (aspartate and glutamate) along with the original wild-type residue (wt) in every combination across 15 residues in the anti-RNase A VHH binding interface (FIG. 19). M13 Phage displaying the library of Asp/Glu/Wt VHH variants, were generated as described for the combinatorial histidine-scanning library (Example 1). VHH displaying phage were produced, selected for RNase A target binding, and characterized for "inverse" pH dependence properties, i.e., decreased affinity with increasing pH (FIG. 18). VHH variants were tested for binding at pH 4. and at pH 8.0 (FIG. 19). Based on ELISA screening, Variant-3, which introduced seven new acidic residues across the CDR1 and CDR3 interface loops, was identified as an inverse pH-sensitive VHH clone (Table 5).

TABLE 1

Thermodynamic ITC data for RNAse A binding VHH#10 and VHH#24, respectively, at 25° C.

| pH | Buffer | $\Delta H_{ion}$ (kcal/mol)[a,b] | n | $\Delta H$ (kcal/mol) | $-T\Delta S$ (kcal/mol) | $\Delta G$ (kcal/mol) | $K_d$ (µM) |
|---|---|---|---|---|---|---|---|
| VHH 10 | | | | | | | |
| 4.54 | Piperazine | 7.44 | 1.00[c] | −44.71 ± 6 | 40 ± 6 | −4.46 ± 0.11 | 530 ± 30 |
| 4.74 | Piperazine | 7.44 | 1.00[c] | −17.61 ± 0.6 | 12.4 ± 0.6 | −5.20 ± 0.04 | 150 ± 30 |
| 5 | Piperazine | 7.44 | 1.00[c] | −10.82 ± 0.5 | 4.7 ± 0.5 | −6.11 ± 0.06 | 33 ± 4.0 |
| 5.5 | Acetate | 0.12 | 1.01 | 1.33 ± 0.05 | −8.7 ± 0.1 | −7.41 ± 0.08 | 3.6 ± 0.3 |
| 6 | PBS | 1.22 | 0.96 | −2.68 ± 0.09 | −5 ± 0.1 | −7.76 ± 0.09 | 2.0 ± 0.2 |
| 6.5 | Imidazole | 8.75 | 0.99 | −17.29 ± 0.07 | 7.8 ± 0.08 | −9.45 ± 0.03 | 0.1 ± 0.02 |
| 7 | PBS | 1.22 | 1.00 | −11.41 ± 0.08 | 1.4 ± 0.09 | −10.02 ± 0.05 | 0.04 ± 0.005 |
| 7.4 | PBS | 1.22 | 0.97 | −13.85 ± 0.06 | 3.7 ± 0.08 | −10.18 ± 0.05 | 0.03 ± 0.004 |
| 8 | TRIS | 11.3 | 0.97 | −16.21 ± 0.05 | 6 ± 0.06 | −10.20 ± 0.04 | 0.03 ± 0.006 |
| VHH 24 | | | | | | | |
| 4.5 | Piperazine | 7.44 | 1.00[c] | −30 ± 3 | 25.36 ± 3 | −5.11 ± 0.11 | 18 ± 0.01 |
| 4.74 | Piperazine | 7.44 | 1.00[c] | −12.45 ± 0.6 | 6.8 ± 0.6 | −5.62 ± 0.05 | 75 ± 8.0 |
| 5 | Piperazine | 7.44 | 1.00[c] | −4.8 ± 0.07 | −2.4 ± .08 | −7.03 ± 0.25 | 12 ± 3.0 |
| 5.5 | Acetate | 0.12 | 1.05 | 3.0 ± 0.2 | 10 ± 0.3 | −7.09 ± 0.14 | 6.3 ± 0.3 |
| 6 | PBS | 1.22 | 1.05 | 1.5 ± 0.05 | −8.6 ± 0.07 | −7.07 ± 0.06 | 6.5 ± 0.7 |
| 6.5 | Imidazole | 8.75 | 0.96 | −9.44 ± 0.2 | −8.6 ± 0.7 | −8.73 ± 0.09 | 0.4 ± 0.03 |
| 7 | PBS | 1.22 | 1 | −4.35 ± 0.05 | 0.7 ± 0.2 | −9.07 ± 0.06 | 0.2 ± 0.02 |
| 7.4 | PBS | 1.22 | 0.995 | −6.84 ± 0.08 | −2.5 ± 0.1 | −9.31 ± 0.08 | 0.2 ± 0.01 |
| 8 | TRIS | 11.3 | 1.03 | −9.00 ± 0.07 | −3.8 ± 0.09 | −9.37 ± 0.05 | 0.1 ± 0.01 |

TABLE 2

Crystallography statistics for the VHH#24/RNase A complex

| Data collection | |
|---|---|
| Space group | P12$_1$1 |
| a, b, c | 40.79, 54.68, 48.79 |
| α, β, γ | 90, 109.24, 90 |

TABLE 2-continued

Crystallography statistics for the VHH#24/RNase A complex

| | |
|---|---|
| Resolution range | 20-1.75 Å |
| Number of reflections | 176379 |
| I/σ | 21.46 |
| $R_{merge}$ | 0.047 |
| Completeness (%) | 99.9 |
| Redundancy | 3.7 |
| Refinement | |
| $R_{work}/R_{free}$ | 19.08/24.47 |
| Average residue/chain | |
| VHH | 123 |
| RNase A | 129 |
| Water | 91 |

TABLE 2-continued

Crystallography statistics for the VHH#24/RNase A complex

| | |
|---|---|
| RMSD | |
| Bond lengths (Å) | 0.0147 |
| Bond angles (°) | 1.5242 |
| Chiral volume | 0.1083 |
| Ramachandran plot statistics | |
| Preferred (%) | 229 (97.86) |
| Additional allowed (%) | 3 (1.28) |
| Outliers (%) | 2 (0.85) |

TABLE 3

ITC data for all Metal-VHH binding experiments at 25° C.

| Target | N | ΔH° kcal/mol | −TΔS° kcal/mol | ΔG° kcal/mol | K | Kd μM |
|---|---|---|---|---|---|---|
| Nickel | 1.01 ± 0.02 | −12.1 ± 1.5 | 6 ± 1 | −6.1 ± 0.2 | 3 ± 1 × 10⁴ | 30 ± 10 |
| RNase A | 0.96 ± 0.01 | −17.8 ± 0.1 | 9.0 ± 0.1 | −9.3 ± 0.01 | 6.4 ± 0.1 × 10⁶ | 0.157 ± 0.003 |
| 1 μM Nickel Competitive | 0.959 ± 0.002 | −17.20 ± 0.08 | 8.0 ± 0.8 | −9.27 ± 0.06 | 6.3 ± 0.6 × 10⁶ | 0.160 ± 0.002 |
| 10 μM Nickel Competitive | 0.98 ± 0.01 | −12.70 ± 0.02 | 3.6 ± 0.2 | −9.10 ± 0.08 | 4.6 ± 0.6 × 10⁶ | 0.219 ± 0.003 |
| 100 μM Nickel Competitive | 0.98 ± 0.03 | −7 ± 1 | −1 ± 1 | −8.27 ± 0.06 | 1.2 ± 0.1 × 10⁶ | 0.9 ± 0.1 |
| 1 mM Nickel Competitive | 1.00* | −7.2 ± 0.2 | 0.09 ± 1 | −7.13 ± 0.04 | 1.3 ± 0.1 × 10⁵ | 5.64 ± 0.4 |
| 10 mM Nickel Competitive | 1.00* | −7.3 ± 0.2 | 1.3 ± 0.2 | −6.07 ± 0.01 | 2.9 ± 0.4 × 10⁴ | 34.00 ± 0.05 |

TABLE 4

ITC data for Wild-Type anti-RNaseA binding to RNase A at 25° C.

| Target | N | ΔH° kcal/mol | −TΔS° kcal/mol | ΔG° kcal/mol | K | Kd nM |
|---|---|---|---|---|---|---|
| RNase A | 1.010 ± 0.008 | −12.4 ± 0.2 | 1.9 ± 0.2- | −10.51 ± 0.07 | 5 ± 1 × 10⁷ | 19 ± 1 |
| 1 mM Nickel Competitive | 0.994 ± 0.005 | −10.70 ± 0.08 | 0.90 ± 0.08 | −10.60 ± 0.01 | 6.1 ± 0.7 × 10⁷ | 16 ± 1 |

TABLE 5

Amino acid sequences of the CDR1 and CDR3 loops from wt anti-RNase A VHH and the pH-sensitive VHH Variant-3.
Seven positions were observed to acquire a new acidic residue (aspartate or glutamate).
Table discloses SEQ ID NOS 45-48, respectively, in order of appearance.

| | CDR1 Residues | | | | | | | | CDR1 Residues | | | | | | | | |
|---|---|---|---|---|---|---|---|---|---|---|---|---|---|---|---|---|---|
| VHH | 26 | 27 | 28 | 29 | 39 | 31 | 32 | 33 | 101 | 102 | 103 | 104 | 105 | 106 | 107 | 108 | 109 | 110 |
| Wt | G | Y | A | Y | T | Y | I | Y | Y | E | L | R | D | R | T | Y | G | Q |
| Variant-3 | G | D | A | E | D | Y | V | D | D | D | L | G | E | G | D | Y | G | E |

DOCUMENTS CITED

The following documents are incorporated by reference to the extent they relate to or describe materials or methods disclosed herein.

Cunningham B C, Wells J A (1989) Science 244:1081-1085.

Decanniere K, et al. (1999) Structure 7, 361-370.

Fellouse F A et al. (2007), J Mol Biol 373:924-940.

Franco E J et al. (2010) J. Chromatography B, 878: 177-186.

Hoogenboom H (2006) Nature Biotechnol. 23: 1105-1116.

Isom D G et al. (2008) Proc Natl Acad Sci USA 105: 17784-17788.

Isom D G et al. (2011) Proc Natl Acad Sci USA 108: 5260-5265.

Isom D G et al. (2010) Proc Natl Acad Sci USA 107: 16096-16100

Koide A et al. (2007) J Mol Biol 373, 941-953

Kunkel T A et al. (1987) Methods Enzymol 154: 367-382.

Lipovsek D, Pluckthun A (2004) J Immunol Methods 290:51-67.

Otwinowski Z, Minor W (1997) Methods Enzymol 276: 307-326.

Pace C N et al., (1995) Protein Sci 4, 2411-2423.

Sidhu S S, Weiss G A (2004) Constructing phage display libraries by olignucleotide-directed mutagenesis, in Phage Display: a practical approach (Clarkson, T., and Lowman, H. B., Eds.) pp. 27-41, Oxford university Press, Oxford.

Sonneson G J, Horn J R (2009) Biochemistry 48, 6693-6695.

Turnbull W B, Daranas A H (2003) J Am Chem Soc 125, 14859-14866.

---

The invention claimed is:

1. A method for introducing molecular switch functionality into a wild type antibody that binds a target molecule via a target binding interface, the method comprising:

(a) obtaining a combinatorial ionizable residue-scanning protein display library of the antibody, the library comprising all possible combinations of amino acid residues of the target binding interface wherein each residue position was modified as an ionizable amino acid residue, and the remaining positions maintain residues in the;

(b) selecting a target binding population of antibodies from the library based on their ability to bind the target molecule;

(c) selecting a target binding subpopulation from the target binding population that exhibits binding to the target molecule sensitive to the environmental trigger; and (d) identifying a modified antibody from the subpopulation with molecular switch functionality sensitive to the environmental trigger while maintaining binding affinity to the target molecule, wherein the environmental trigger is a specific pH selected from a predetermined range.

2. The method of claim 1, wherein the antibody is a heavy chain variable domain antibody (VHH).

3. The method of claim 1, wherein the target molecule is selected from a group consisting of a protein, DNA, and carbohydrates.

4. The method of claim 1, wherein the modification of the amino acids is done by substitution.

5. The method of claim 1, further comprising:

(e) producing the antibody in a BL21(DE3) expression system.

6. The method of claim 1, wherein the predetermined range of pH is between about 4 and about 8.

7. The method of claim 1, wherein the predetermined range of pH is between 4 and 7.4.

8. The method of claim 1, wherein the specific pH is 7.4.

9. The method of claim 1, wherein the specific pH is about 5.

* * * * *

SEQUENCE LISTING

```
<160> NUMBER OF SEQ ID NOS: 48

<210> SEQ ID NO 1
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgtctgagct gcgcagcaag csrtyatsmt yatmmtyatm wtyatmwksr ttggttccgt    60
caagcaccag g                                                         71

<210> SEQ ID NO 2
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cctactactg cgcagcasrt srtyatsawc wtcrtsatcr tmmtyatsrt cawtggggtc    60
aaggcaccc                                                            69

<210> SEQ ID NO 3
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagatataca tatgcatcat catcatcatc atgaaaacct gtacttccag ggatcccaag    60
tacaactggt ag                                                        72

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```
tagactcgag gaattcctat tagctgctta cggttacttg g    41

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 6

His His His His His
1               5

<210> SEQ ID NO 7
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 7

Gly Tyr Ala Tyr Thr Tyr Ile Tyr Met Gly
1               5                   10

<210> SEQ ID NO 8
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 8

Gly Tyr Asp His Thr Tyr Ile Tyr Met Gly
1               5                   10

<210> SEQ ID NO 9
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 9

Gly His Ala His Thr Tyr Leu His Met Gly
1               5                   10

<210> SEQ ID NO 10
<211> LENGTH: 10
<212> TYPE: PRT
<213> ORGANISM: Unknown
<220> FEATURE:

```
<223> OTHER INFORMATION: Description of Unknown: Camelid
      VHH CDR1 peptide

<400> SEQUENCE: 10

His His Pro Tyr Pro Tyr Ile Tyr Met Gly
1               5                   10

<210> SEQ ID NO 11
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 11

Arg Tyr Asp His Thr Tyr Leu His Met Gly
1               5                   10

<210> SEQ ID NO 12
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 12

Gly Tyr Asp Tyr Thr Tyr His His Met Gly
1               5                   10

<210> SEQ ID NO 13
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 13

Gly Tyr Ala His Pro Tyr Leu His Met Gly
1               5                   10

<210> SEQ ID NO 14
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 14

Asp Tyr His His Pro Tyr Leu Tyr Met Gly
1               5                   10

<210> SEQ ID NO 15
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 15

Asp His Asp His Pro Tyr Ile Tyr Met Gly
1               5                   10
```

```
<210> SEQ ID NO 16
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 16

Gly Tyr Pro His Pro Tyr Leu His Met Gly
1               5                   10

<210> SEQ ID NO 17
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 17

Gly Tyr His His Pro Tyr Ile Tyr Met Gly
1               5                   10

<210> SEQ ID NO 18
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 18

Arg His Ala Tyr Pro Tyr Leu Tyr Met Gly
1               5                   10

<210> SEQ ID NO 19
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 19

Gly His Asp His Pro Tyr Leu His Met Gly
1               5                   10

<210> SEQ ID NO 20
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 20

Gly His Pro His Pro Tyr Ile Tyr Met Gly
1               5                   10

<210> SEQ ID NO 21
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 21
```

```
Gly His Pro Tyr Thr Tyr Leu His Met Gly
1               5                   10

<210> SEQ ID NO 22
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 22

Gly Tyr Asp His Pro Tyr Leu Tyr Met Gly
1               5                   10

<210> SEQ ID NO 23
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 23

Gly Tyr Pro His Pro Tyr Leu Tyr Met Gly
1               5                   10

<210> SEQ ID NO 24
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 24

Asp Tyr Asp His Thr Tyr Ile Tyr Met Gly
1               5                   10

<210> SEQ ID NO 25
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 25

Asp Tyr Pro His Pro Tyr Leu Tyr Met Gly
1               5                   10

<210> SEQ ID NO 26
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 26

Arg Tyr Pro His Pro Tyr Leu His Met Gly
1               5                   10

<210> SEQ ID NO 27
<211> LENGTH: 10
<212> TYPE: PRT
<213> ORGANISM: Unknown
```

```
<220> FEATURE:
<223> OTHER INFORMATION: Description of Unknown: Camelid
      VHH CDR1 peptide

<400> SEQUENCE: 27

Gly Tyr Ala His Thr Tyr Thr His Met Gly
1               5                   10

<210> SEQ ID NO 28
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 28

Gly Tyr Ala His Thr Tyr Thr Tyr Met Gly
1               5                   10

<210> SEQ ID NO 29
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 29

Gly Tyr Ala His Thr Tyr His His Met Gly
1               5                   10

<210> SEQ ID NO 30
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 30

Asp Tyr Pro His Thr Tyr Thr His Met Gly
1               5                   10

<210> SEQ ID NO 31
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 31

Gly Tyr Ala Tyr Thr Tyr Leu His Met Gly
1               5                   10

<210> SEQ ID NO 32
<211> LENGTH: 10
<212> TYPE: PRT
<213> ORGANISM: Unknown
<220> FEATURE:
<223> OTHER INFORMATION: Description of Unknown: Camelid
      VHH CDR1 peptide

<400> SEQUENCE: 32

Arg Tyr Asp Tyr Thr Tyr His His Met Gly
1               5                   10
```

```
<210> SEQ ID NO 33
<211> LENGTH: 12
<212> TYPE: PRT
<213> ORGANISM: Unknown
<220> FEATURE:
<223> OTHER INFORMATION: Description of Unknown: Camelid
      VHH CDR3 peptide

<400> SEQUENCE: 33

Gly Gly Tyr Glu Leu Arg Asp Arg Thr Tyr Gly Gln
1               5                   10

<210> SEQ ID NO 34
<211> LENGTH: 12
<212> TYPE: PRT
<213> ORGANISM: Unknown
<220> FEATURE:
<223> OTHER INFORMATION: Description of Unknown: Camelid
      VHH CDR3 peptide

<400> SEQUENCE: 34

Gly Gly His Glu Leu Arg Asp Arg Thr Tyr Gly Gln
1               5                   10

<210> SEQ ID NO 35
<211> LENGTH: 12
<212> TYPE: PRT
<213> ORGANISM: Unknown
<220> FEATURE:
<223> OTHER INFORMATION: Description of Unknown: Camelid
      VHH CDR3 peptide

<400> SEQUENCE: 35

Gly Gly Tyr Gln Leu Arg Asp Arg Thr Tyr Gly Gln
1               5                   10

<210> SEQ ID NO 36
<211> LENGTH: 12
<212> TYPE: PRT
<213> ORGANISM: Unknown
<220> FEATURE:
<223> OTHER INFORMATION: Description of Unknown: Camelid
      VHH CDR3 peptide

<400> SEQUENCE: 36

Gly Gly Tyr Gln Leu Arg Asp Arg Thr Tyr Gly His
1               5                   10

<210> SEQ ID NO 37
<211> LENGTH: 12
<212> TYPE: PRT
<213> ORGANISM: Unknown
<220> FEATURE:
<223> OTHER INFORMATION: Description of Unknown: Camelid
      VHH CDR3 peptide

<400> SEQUENCE: 37

Gly Gly His His Leu Arg Asp His Thr Tyr Gly Gln
1               5                   10

<210> SEQ ID NO 38
<211> LENGTH: 12
<212> TYPE: PRT
<213> ORGANISM: Unknown
<220> FEATURE:
<223> OTHER INFORMATION: Description of Unknown: Camelid
      VHH CDR3 peptide
```

```
<400> SEQUENCE: 38

Gly Gly His Glu Leu Arg Asp Arg Thr Tyr Gly His
1               5                   10

<210> SEQ ID NO 39
<211> LENGTH: 12
<212> TYPE: PRT
<213> ORGANISM: Unknown
<220> FEATURE:
<223> OTHER INFORMATION: Description of Unknown: Camelid
      VHH CDR3 peptide

<400> SEQUENCE: 39

Gly Gly Tyr Glu Leu Arg Asp His Thr Tyr Gly Gln
1               5                   10

<210> SEQ ID NO 40
<211> LENGTH: 12
<212> TYPE: PRT
<213> ORGANISM: Unknown
<220> FEATURE:
<223> OTHER INFORMATION: Description of Unknown: Camelid
      VHH CDR3 peptide

<400> SEQUENCE: 40

Gly Gly His Glu Leu Arg Asp His Thr Tyr Gly Gln
1               5                   10

<210> SEQ ID NO 41
<211> LENGTH: 12
<212> TYPE: PRT
<213> ORGANISM: Unknown
<220> FEATURE:
<223> OTHER INFORMATION: Description of Unknown: Camelid
      VHH CDR3 peptide

<400> SEQUENCE: 41

Gly Gly His Asp Leu His Asp Arg Thr Tyr Gly Gln
1               5                   10

<210> SEQ ID NO 42
<211> LENGTH: 12
<212> TYPE: PRT
<213> ORGANISM: Unknown
<220> FEATURE:
<223> OTHER INFORMATION: Description of Unknown: Camelid
      VHH CDR3 peptide

<400> SEQUENCE: 42

Gly Gly Tyr Gln Leu Arg Asp His Thr Tyr Gly Gln
1               5                   10

<210> SEQ ID NO 43
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Ser Gln Val Gln Leu Val Glu Ser Gly Gly Leu Val Gln Ala
1               5                   10                  15

Gly Gly Ser Leu Arg Leu Ser Cys Ala Ala Ser Gly Tyr Ala Tyr Thr
            20                  25                  30

Tyr Ile Tyr Met Gly Trp Phe Arg Gln Ala Pro Gly Lys Glu Arg Glu
```

```
            35                  40                  45
Gly Val Ala Ala Met Asp Ser Gly Gly Gly Thr Leu Tyr Ala Asp
        50                  55                  60
Ser Val Lys Gly Arg Phe Thr Ile Ser Arg Asp Lys Gly Lys Asn Thr
 65                  70                  75                  80
Val Tyr Leu Gln Met Asp Ser Leu Lys Pro Glu Asp Thr Ala Thr Tyr
                 85                  90                  95
Tyr Cys Ala Ala Gly Gly Tyr Glu Leu Arg Asp Arg Thr Tyr Gly
            100                 105                 110
Gln Trp Gly Gln Gly Thr Gln Val Thr Val Ser Ser
            115                 120
```

<210> SEQ ID NO 44
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Gly Ser Gln Val Gln Leu Val Glu Ser Gly Gly Gly Leu Val Gln Ala
 1               5                   10                  15
Gly Gly Ser Leu Arg Leu Ser Cys Ala Ala Ser Gly Tyr Pro His Pro
            20                  25                  30
Tyr Leu His Met Gly Trp Phe Arg Gln Ala Pro Gly Lys Glu Arg Glu
        35                  40                  45
Gly Val Ala Ala Met Asp Ser Gly Gly Gly Thr Leu Tyr Ala Asp
        50                  55                  60
Ser Val Lys Gly Arg Phe Thr Ile Ser Arg Asp Lys Gly Lys Asn Thr
 65                  70                  75                  80
Val Tyr Leu Gln Met Asp Ser Leu Lys Pro Glu Asp Thr Ala Thr Tyr
                 85                  90                  95
Tyr Cys Ala Ala Gly Gly Tyr Gln Leu Arg Asp Arg Thr Tyr Gly
            100                 105                 110
His Trp Gly Gln Gly Thr Gln Val Thr Val Ser Ser
            115                 120
```

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Gly Tyr Ala Tyr Thr Tyr Ile Tyr
 1               5
```

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Tyr Glu Leu Arg Asp Arg Thr Tyr Gly Gln
 1               5                   10
```

-continued

```
<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Asp Ala Glu Asp Tyr Val Asp
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Asp Leu Gly Glu Gly Asp Tyr Gly Glu
1               5                   10
```